US009045517B2

(12) United States Patent
    Yang

(10) Patent No.: US 9,045,517 B2
(45) Date of Patent: Jun. 2, 2015

(54) GLYCOSYLATED AMINOCOUMARINS AND METHODS OF PREPARING AND USES OF SAME

(75) Inventor: Min Yang, London (GB)

(73) Assignee: University College London, London (GB)

( * ) Notice: Subject to any disclaimer, the term of this patent is extended or adjusted under 35 U.S.C. 154(b) by 123 days.

(21) Appl. No.: 13/879,071

(22) PCT Filed: Oct. 17, 2011

(86) PCT No.: PCT/GB2011/052006
    § 371 (c)(1),
    (2), (4) Date: Jun. 20, 2013

(87) PCT Pub. No.: WO2012/049521
    PCT Pub. Date: Apr. 19, 2012

(65) Prior Publication Data
    US 2013/0274213 A1    Oct. 17, 2013

(30) Foreign Application Priority Data
    Oct. 15, 2010    (GB) .................................. 1017450.6

(51) Int. Cl.
    *C07H 17/04*     (2006.01)
    *C12P 19/60*     (2006.01)
    *C07H 17/075*    (2006.01)

(52) U.S. Cl.
    CPC .............. *C07H 17/04* (2013.01); *C07H 17/075* (2013.01); *C12P 19/605* (2013.01)

(58) Field of Classification Search
    None
    See application file for complete search history.

(56) References Cited

U.S. PATENT DOCUMENTS 3,153,035 A * 10/1964 Archer et al. ................ 536/17.9
3,547,903 A * 12/1970 Hooper et al. ............... 536/17.4

FOREIGN PATENT DOCUMENTS

WO    WO-01/87309 A1    11/2001
WO    WO-2006/003456 A2    1/2006

OTHER PUBLICATIONS

Patel et al. Chem Commun., 2011, 47, 10569-10571.*
Keegstra et al. Current Opinion in Plant Biology 2001, 4:219-224.*
Lao et al. The Plant Journal (2014) 79, 517-529.*
Yang, M. et al. "Probing the Breadth of Macrolide Glycosyltransferases: In Vitro Remodeling of a Polyketide Antibiotic Creates Active Bacterial Uptake and Enhances Potency" *Journal of the American Chemical Society*, Jul. 6, 2005, 127:9336-9337.
International Search Report in International Application No. PCT/GB2011/052006, filed Oct. 17, 2011.

* cited by examiner

*Primary Examiner* — Layla Bland
(74) *Attorney, Agent, or Firm* — Saliwanchik, Lloyd & Eisenschenk

(57) ABSTRACT

There is provided a method of glycosylating an aminocoumarin compound comprising conjugating a sugar to the 4'-OH position of the core of the aminocoumarin compound. Also provided is an aminocoumarin compound glycosylated at the 4'-OH position of the core of the aminocoumarin compound. Further aspects of this invention provide this compound for use in therapy, more particularly for use as an antibiotic, or in anticancer treatment.

5 Claims, 5 Drawing Sheets

(a)

(b)

(c)

SEQUENCE LISTING

<160> NUMBER OF SEQ ID NOS: 26

<210> SEQ ID NO 1
<211> LENGTH: 1383
<212> TYPE: DNA
<213> ORGANISM: Arabidopsis thaliana

<400> SEQUENCE: 1

```
atgaccaaac cctccgaccc aaccagagac tcccacgtgg cagttctcgc ttttcctttc      60
ggcactcatg cagctcctct cctcaccgtc acgcgccgcc tcgcctccgc ctctccttcc     120
accgtcttct ctttcttcaa caccgcacaa tccaactctt cgttattttc ctccggtgac     180
gaagcagatc gtccggcgaa catcagagta tacgatattg ccgacggtgt tccggaggga     240
```

-continued

```
tacgtgttta gcgggagacc acaggaggcg atcgagctgt tcttcaagc tgcgccggag    300
aatttccgga gagaaatcgc gaaggcgag acggaggttg gtacggaagt gaaatgtttg    360
atgactgatg cgttcttctg gttcgcggct gatatggcga cggagataaa tgcgtcgtgg    420
attgcgtttt ggaccgccgg agcaaactca ctctctgctc atctctacac agatctcatc    480
agagaaacca tcggtgtcaa agaagtaggt gagcgtatgg aggagacaat aggggttatc    540
tcaggaatgg agaagatcag agtcaaagat acaccagaag gagttgtgtt tgggaattta    600
gactctgttt tctcaaagat gcttcatcaa atgggtcttg ctttgcctcg tgccactgct    660
gttttcatca attcttttga agatttggat cctacattga cgataaccct cagatcgaga    720
tttaaacgat atctgaacat cggtcctctc gggttattat cttctacatt gcaacaacta    780
gtgcaagatc ctcacggttg tttggcttgg atggagaaga gatcttctgg ttctgtggcg    840
tacattagct ttggtacggt catgacaccg cctcctggag agcttgcggc gatagcagaa    900
gggttggaat cgagtaaagt gccgtttgtt tggtcgctta aggagaagag cttggttcag    960
ttaccaaaag ggttttttgga taggacaaga gagcaaggga tagtggttcc atgggcaccg    1020
caagtggaac tgctgaaaca cgaagcaacg ggtgtgtttg tgacgcattg tggatggaac    1080
tcggtgttgg agagtgtatc gggtggtgta ccgatgattt gcaggccatt tttgggat    1140
cagagattga acggaagagc ggtggaggtt gtgtgggaga ttggaatgac gattatcaat    1200
ggagtcttca cgaaagatgg gtttgagaag tgtttggata agtttttagt tcaagatgat    1260
ggtaagaaga tgaaatgtaa tgctaagaaa cttaagaac tagcttacga agctgtctct    1320
tctaaaggaa ggtcctctga gaatttcaga ggattgttgg atgcagttgt aaacattatt    1380
tga                                                                  1383
```

```
<210> SEQ ID NO 2
<211> LENGTH: 460
<212> TYPE: PRT
<213> ORGANISM: Arabidopsis thaliana

<400> SEQUENCE: 2

Met Thr Lys Pro Ser Asp Pro Thr Arg Asp Ser His Val Ala Val Leu
 1               5                  10                  15

Ala Phe Pro Phe Gly Thr His Ala Ala Pro Leu Leu Thr Val Thr Arg
            20                  25                  30

Arg Leu Ala Ser Ala Ser Pro Ser Thr Val Phe Ser Phe Asn Thr
        35                  40                  45

Ala Gln Ser Asn Ser Ser Leu Phe Ser Ser Gly Asp Glu Ala Asp Arg
    50                  55                  60

Pro Ala Asn Ile Arg Val Tyr Asp Ile Ala Asp Gly Val Pro Glu Gly
65                  70                  75                  80

Tyr Val Phe Ser Gly Arg Pro Gln Glu Ala Ile Glu Leu Phe Leu Gln
                85                  90                  95

Ala Ala Pro Glu Asn Phe Arg Arg Glu Ile Ala Lys Ala Glu Thr Glu
            100                 105                 110

Val Gly Thr Glu Val Lys Cys Leu Met Thr Asp Ala Phe Phe Trp Phe
        115                 120                 125

Ala Ala Asp Met Ala Thr Glu Ile Asn Ala Ser Trp Ile Ala Phe Trp
    130                 135                 140

Thr Ala Gly Ala Asn Ser Leu Ser Ala His Leu Tyr Thr Asp Leu Ile
145                 150                 155                 160

Arg Glu Thr Ile Gly Val Lys Glu Val Gly Glu Arg Met Glu Glu Thr
```

```
                165                 170                 175
Ile Gly Val Ile Ser Gly Met Glu Lys Ile Arg Val Lys Asp Thr Pro
            180                 185                 190
Glu Gly Val Val Phe Gly Asn Leu Asp Ser Val Phe Ser Lys Met Leu
            195                 200                 205
His Gln Met Gly Leu Ala Leu Pro Arg Ala Thr Ala Val Phe Ile Asn
            210                 215                 220
Ser Phe Glu Asp Leu Asp Pro Thr Leu Thr Asn Asn Leu Arg Ser Arg
225                 230                 235                 240
Phe Lys Arg Tyr Leu Asn Ile Gly Pro Leu Gly Leu Leu Ser Ser Thr
                245                 250                 255
Leu Gln Gln Leu Val Gln Asp Pro His Gly Cys Leu Ala Trp Met Glu
            260                 265                 270
Lys Arg Ser Ser Gly Ser Val Ala Tyr Ile Ser Phe Gly Thr Val Met
            275                 280                 285
Thr Pro Pro Pro Gly Glu Leu Ala Ala Ile Ala Glu Gly Leu Glu Ser
            290                 295                 300
Ser Lys Val Pro Phe Val Trp Ser Leu Lys Glu Lys Ser Leu Val Gln
305                 310                 315                 320
Leu Pro Lys Gly Phe Leu Asp Arg Thr Arg Glu Gln Gly Ile Val Val
                325                 330                 335
Pro Trp Ala Pro Gln Val Glu Leu Leu Lys His Glu Ala Thr Gly Val
            340                 345                 350
Phe Val Thr His Cys Gly Trp Asn Ser Val Leu Glu Ser Val Ser Gly
            355                 360                 365
Gly Val Pro Met Ile Cys Arg Pro Phe Phe Gly Asp Gln Arg Leu Asn
            370                 375                 380
Gly Arg Ala Val Glu Val Val Trp Glu Ile Gly Met Thr Ile Ile Asn
385                 390                 395                 400
Gly Val Phe Thr Lys Asp Gly Phe Glu Lys Cys Leu Asp Lys Val Leu
                405                 410                 415
Val Gln Asp Asp Gly Lys Lys Met Lys Cys Asn Ala Lys Lys Leu Lys
            420                 425                 430
Glu Leu Ala Tyr Glu Ala Val Ser Ser Lys Gly Arg Ser Ser Glu Asn
            435                 440                 445
Phe Arg Gly Leu Leu Asp Ala Val Val Asn Ile Ile
            450                 455                 460

<210> SEQ ID NO 3
<211> LENGTH: 1422
<212> TYPE: DNA
<213> ORGANISM: Arabidopsis thaliana

<400> SEQUENCE: 3
atgaaagtag aacttgtgtt cataccatcg ccgggcgttg gccatatccg agcaacaacg      60
gcgttagcaa agcttctcgt tgccagcgac aaccgcctct ccgtcactct catcgtcatt     120
ccttcacgag tctccgacga cgcttcttcc tccgtctaca cgaactccga agaccgtctc     180
cgctacatcc tcctccccgc ccgagatcaa actactgatc tcgtatctta catcgacagc     240
cagaaaccac aagtaagagc cgtcgtgtcc aaggtcgctg agatgtttca acacgttca      300 gactcacggc tagctgggat tgtcgtagac atgttctgca cgtccatgat agacatcgcc     360
gatgagttta acctctcggc ttatatcttc tacacgtcca acgcttctta ctctcgggcta    420 cagttccacg ttcaatctct ttacgacgag aaagaactcg acgtaagtga gttcaaagat    480
```

```
acggagatga agtttgacgt tccaactctg actcagcctt ttccggcaaa atgtttgcct    540
tcagtgatgc taaacaagaa atggtttcct tacgttttgg gtcgagctag aagttttaga    600
gcaacgaagg gtattttggt aaattcggtg gctgacatgg aacctcaggc gttgagtttc    660
ttttccggtg gaaatgggaa tacaaatatc cctccggtgt acgcggttgg gcccattatg    720
gacttagaat ctagcggcga tgaagagaag agaaaggaga tttttacattg gctaaaagag    780 caaccgacga aatctgtagt gtttctctgt tttgggagca tgggaggttt cagtgaggaa    840
caagcaagag aaatagctgt ggcgctcgag cgaagcggac acaggtttct ctggtcgctt    900
cgccgcgctt ctcctgttgg aaacaagtct aatcctcctc ccggagaatt cacgaactta    960
gaggagattc ttccaaaagg ttttttagat cggacggtgg agatagggaa gatcataagc   1020
tgggcaccac aagtagatgt gttgaatagt cctgctatag gagcgttcgt gacacattgt   1080
ggatggaact caattctcga gagtctttgg ttcggtgttc cgatggcggc gtggcctatc   1140
tatgctgagc aacagtttaa cgcgtttcat atggtggatg agcttggttt agcggcggag   1200
gtaaagaagg agtaccgtag agattttctg gtggaggagc cggagattgt gacggctgat   1260
gagatagaga gagggatcaa gtgtgcgatg gagcaggata gcaagatgag gaagagggtg   1320
atggagatga aggataagct ccacgtggcg ttggtggacg gtggatcttc gaactgtgct   1380
ctaaagaagt tgttcaaga cgtggtcgat aatgttccat aa                        1422
```

<210> SEQ ID NO 4
<211> LENGTH: 473
<212> TYPE: PRT
<213> ORGANISM: Arabidopsis thaliana

<400> SEQUENCE: 4

```
Met Lys Val Glu Leu Val Phe Ile Pro Ser Pro Gly Val Gly His Ile
1               5                   10                  15

Arg Ala Thr Thr Ala Leu Ala Lys Leu Leu Val Ala Ser Asp Asn Arg
            20                  25                  30

Leu Ser Val Thr Leu Ile Val Ile Pro Ser Arg Val Ser Asp Asp Ala
        35                  40                  45

Ser Ser Ser Val Tyr Thr Asn Ser Glu Asp Arg Leu Arg Tyr Ile Leu
    50                  55                  60

Leu Pro Ala Arg Asp Gln Thr Thr Asp Leu Val Ser Tyr Ile Asp Ser
65                  70                  75                  80

Gln Lys Pro Gln Val Arg Ala Val Val Ser Lys Val Ala Gly Asp Val
                85                  90                  95

Ser Thr Arg Ser Asp Ser Arg Leu Ala Gly Ile Val Val Asp Met Phe
            100                 105                 110

Cys Thr Ser Met Ile Asp Ile Ala Asp Glu Phe Asn Leu Ser Ala Tyr
        115                 120                 125

Ile Phe Tyr Thr Ser Asn Ala Ser Tyr Leu Gly Leu Gln Phe His Val
    130                 135                 140

Gln Ser Leu Tyr Asp Glu Lys Glu Leu Asp Val Ser Glu Phe Lys Asp
145                 150                 155                 160

Thr Glu Met Lys Phe Asp Val Pro Thr Leu Thr Gln Pro Phe Pro Ala
                165                 170                 175

Lys Cys Leu Pro Ser Val Met Leu Asn Lys Lys Trp Phe Pro Tyr Val
            180                 185                 190

Leu Gly Arg Ala Arg Ser Phe Arg Ala Thr Lys Gly Ile Leu Val Asn
        195                 200                 205
```

Ser Val Ala Asp Met Glu Pro Gln Ala Leu Ser Phe Phe Ser Gly Gly
    210                 215                 220

Asn Gly Asn Thr Asn Ile Pro Pro Val Tyr Ala Val Gly Pro Ile Met
225                 230                 235                 240

Asp Leu Glu Ser Ser Gly Asp Glu Glu Lys Arg Lys Glu Ile Leu His
                245                 250                 255

Trp Leu Lys Glu Gln Pro Thr Lys Ser Val Val Phe Leu Cys Phe Gly
            260                 265                 270

Ser Met Gly Gly Phe Ser Glu Glu Gln Ala Arg Glu Ile Ala Val Ala
        275                 280                 285

Leu Glu Arg Ser Gly His Arg Phe Leu Trp Ser Leu Arg Arg Ala Ser
    290                 295                 300

Pro Val Gly Asn Lys Ser Asn Pro Pro Gly Glu Phe Thr Asn Leu
305                 310                 315                 320

Glu Glu Ile Leu Pro Lys Gly Phe Leu Asp Arg Thr Val Glu Ile Gly
                325                 330                 335

Lys Ile Ile Ser Trp Ala Pro Gln Val Asp Val Leu Asn Ser Pro Ala
            340                 345                 350

Ile Gly Ala Phe Val Thr His Cys Gly Trp Asn Ser Ile Leu Glu Ser
        355                 360                 365

Leu Trp Phe Gly Val Pro Met Ala Ala Trp Pro Ile Tyr Ala Glu Gln
    370                 375                 380

Gln Phe Asn Ala Phe His Met Val Asp Glu Leu Gly Leu Ala Ala Glu
385                 390                 395                 400

Val Lys Lys Glu Tyr Arg Arg Asp Phe Leu Val Glu Glu Pro Glu Ile
                405                 410                 415

Val Thr Ala Asp Glu Ile Glu Arg Gly Ile Lys Cys Ala Met Glu Gln
            420                 425                 430

Asp Ser Lys Met Arg Lys Arg Val Met Glu Met Lys Asp Lys Leu His
        435                 440                 445

Val Ala Leu Val Asp Gly Gly Ser Ser Asn Cys Ala Leu Lys Lys Phe
    450                 455                 460

Val Gln Asp Val Val Asp Asn Val Pro
465                 470

<210> SEQ ID NO 5
<211> LENGTH: 1443
<212> TYPE: DNA
<213> ORGANISM: Arabidopsis thaliana

<400> SEQUENCE: 5

```
atgaacaaat tgcgcttgt cttcgtacca tttcctatac ttggtcatct caaatcaacc      60
gccgagatgg ctaagctact agtggagcaa gaaactcgcc tctctatctc cattatcatc     120
cttcctcttc tttccggaga cgacgtcagt gcttccgctt atatctcagc tctttccgcc     180
gcatccaacg accgccttca ctatgaagtg atctcggacg agatcaacc aaccgtcggg      240 ttacatgtcg ataaccacat cccgatggtg aaacgtaccg ttgcaaaact cgttgatgac     300
tactcaaggc ggccggactc gccgaggctc gctggtttag ttgttgacat gttttgtatc     360
tcggtgatag acgtggctaa tgaggttagt gttccgtgtt acttgtttta cacgtcaaac     420
gttgggattc ttgctcttgg gttacatatt cagatgttgt ttgataagaa ggagtacagt     480
gtcagtgaaa ctgattttga agactcggaa gttgtgttgg atgttccgag tttgacttgt     540
ccttatccgg tgaagtgtct tcctatggt ttggcaacga aagagtggct tcctatgtat      600
```

```
ctaaatcaag gtagaagatt cagagagatg aaaggtattt tggtaaatac ttttgctgag    660
cttgaacctt atgcgttgga gtctcttcac tctagtggtg atactcctcg tgcttatcca    720
gtgggaccat tgttgcatct cgagaaccat gttgacggtt ctaaagacga agggttcg     780
gacattttac ggtggttaga tgaacaacca cctaaatcgg tagtgttcct ctgctttgga    840
agcataggag gctttaacga ggaacaagca agagaaatgg ccattgcact gagagaagt    900
ggtcaccgct tcttgtggtc tcttcgccgt gcatctcgag atatagataa ggaacttccc    960
ggagaattca agaatcttga agaaattctc ccggaaggat tctttgatcg gacaaaggat   1020
aaaggaaagg tgatcggatg ggctccacaa gtagccgtgc tggctaagcc agcaatcgga   1080
ggttttgtta ctcattgcgg gtggaactcg atactcgaga gtctttggtt cggtgttcct   1140
atagcgccat ggccgttata cgctgagcag aagtttaatg ctttcgtgat ggtggaggag   1200
cttggtttgg cagtgaagat aagaaagtat tggcgaggcg atcagttggt gggaacggcg   1260
acggtcatag tgacggcaga ggagatagag agaggaatca gatgtttgat ggagcaagat   1320
agtgacgtga ggaatagagt gaaggagatg agtaagaaat gtcacatggc tttaaaggat   1380
ggtggctcgt ctcaatctgc tttgaaatta tttattcaag acgttacgaa gtatattgct   1440
tga                                                                 1443

<210> SEQ ID NO 6
<211> LENGTH: 480
<212> TYPE: PRT
<213> ORGANISM: Arabidopsis thaliana

<400> SEQUENCE: 6

Met Asn Lys Phe Ala Leu Val Phe Val Pro Phe Pro Ile Leu Gly His
1               5                   10                  15

Leu Lys Ser Thr Ala Glu Met Ala Lys Leu Leu Val Glu Gln Glu Thr
            20                  25                  30

Arg Leu Ser Ile Ser Ile Ile Leu Pro Leu Leu Ser Gly Asp Asp
        35                  40                  45

Val Ser Ala Ser Ala Tyr Ile Ser Ala Leu Ser Ala Ala Ser Asn Asp
    50                  55                  60

Arg Leu His Tyr Glu Val Ile Ser Asp Gly Asp Gln Pro Thr Val Gly
65                  70                  75                  80

Leu His Val Asp Asn His Ile Pro Met Val Lys Arg Thr Val Ala Lys
                85                  90                  95

Leu Val Asp Asp Tyr Ser Arg Arg Pro Asp Ser Pro Arg Leu Ala Gly
            100                 105                 110

Leu Val Val Asp Met Phe Cys Ile Ser Val Ile Asp Val Ala Asn Glu
        115                 120                 125

Val Ser Val Pro Cys Tyr Leu Phe Tyr Thr Ser Asn Val Gly Ile Leu
    130                 135                 140

Ala Leu Gly Leu His Ile Gln Met Leu Phe Asp Lys Lys Glu Tyr Ser
145                 150                 155                 160

Val Ser Glu Thr Asp Phe Glu Asp Ser Glu Val Val Leu Asp Val Pro
                165                 170                 175

Ser Leu Thr Cys Pro Tyr Pro Val Lys Cys Leu Pro Tyr Gly Leu Ala
            180                 185                 190

Thr Lys Glu Trp Leu Pro Met Tyr Leu Asn Gln Gly Arg Arg Phe Arg
        195                 200                 205

Glu Met Lys Gly Ile Leu Val Asn Thr Phe Ala Glu Leu Glu Pro Tyr
```

```
Ala Leu Glu Ser Leu His Ser Ser Gly Asp Thr Pro Arg Ala Tyr Pro
225                 230                 235                 240

Val Gly Pro Leu Leu His Leu Glu Asn His Val Asp Gly Ser Lys Asp
            245                 250                 255

Glu Lys Gly Ser Asp Ile Leu Arg Trp Leu Asp Glu Gln Pro Pro Lys
                260                 265                 270

Ser Val Val Phe Leu Cys Phe Gly Ser Ile Gly Gly Phe Asn Glu Glu
            275                 280                 285

Gln Ala Arg Glu Met Ala Ile Ala Leu Glu Arg Ser Gly His Arg Phe
        290                 295                 300

Leu Trp Ser Leu Arg Arg Ala Ser Arg Asp Ile Asp Lys Glu Leu Pro
305                 310                 315                 320

Gly Glu Phe Lys Asn Leu Glu Glu Ile Leu Pro Glu Gly Phe Phe Asp
                325                 330                 335

Arg Thr Lys Asp Lys Gly Lys Val Ile Gly Trp Ala Pro Gln Val Ala
            340                 345                 350

Val Leu Ala Lys Pro Ala Ile Gly Gly Phe Val Thr His Cys Gly Trp
        355                 360                 365

Asn Ser Ile Leu Glu Ser Leu Trp Phe Gly Val Pro Ile Ala Pro Trp
370                 375                 380

Pro Leu Tyr Ala Glu Gln Lys Phe Asn Ala Phe Val Met Val Glu Glu
385                 390                 395                 400

Leu Gly Leu Ala Val Lys Ile Arg Lys Tyr Trp Arg Gly Asp Gln Leu
                405                 410                 415

Val Gly Thr Ala Thr Val Ile Val Thr Ala Glu Glu Ile Glu Arg Gly
            420                 425                 430

Ile Arg Cys Leu Met Glu Gln Asp Ser Asp Val Arg Asn Arg Val Lys
        435                 440                 445

Glu Met Ser Lys Lys Cys His Met Ala Leu Lys Asp Gly Gly Ser Ser
450                 455                 460

Gln Ser Ala Leu Lys Leu Phe Ile Gln Asp Val Thr Lys Tyr Ile Ala
465                 470                 475                 480

<210> SEQ ID NO 7
<211> LENGTH: 1389
<212> TYPE: DNA
<213> ORGANISM: Arabidopsis thaliana

<400> SEQUENCE: 7
atgggtgaag aagctatagt tctgtatcct gcaccaccaa taggtcactt agtgtccatg     60
gttgagttag gtaaaaccat cctctccaaa aacccatctc tctccatcca cattatctta    120
gttccaccgc ttatcagcc ggaatcaacc gccacttaca tctcctccgt ctcctcctcc     180
ttcccttcaa taaccttcca ccatcttccc gccgtcacac cgtactcctc ctcctccacc    240
tctcgccacc accacgaatc tctcctccta gagatcctct gttttagcaa cccaagtgtc    300
caccgaactc ttttctcact ctctcggaat ttcaatgtcc gagcaatgat catcgatttc    360
ttctgcaccg ccgtttttaga catcaccgct gacttcacgt tcccggttta cttcttctac    420
acctctggag ccgcatgtct cgccttttcc ttctatctcc cgaccatcga cgaaacaacc    480
cccggaaaaa acctcaaaga cattcctaca gttcatatcc ccggcgttcc tccgatgaag    540
ggctccgata tgcctaaggc ggtgctcgaa cgagacgatg aggtctacga tgttttttata    600 atgttcggta acagctctc gaagtcgtca gggattatta tcaatacgtt tgatgcttta    660
```

-continued

```
gaaaacagag ccatcaaggc cataacagag gagctctgtt ttcgcaatat ttatccaatt      720
ggaccgctca ttgtaaacgg aagaatcgaa gatagaaacg acaacaaggc agtttcttgt      780
ctcaattggc tggattcgca gccggaaaag agtgttgtgt ttctctgttt tggaagctta      840
ggtttgttct caaaagaaca ggtgatagag attgctgttg gtttagagaa aagtgggcag      900
agattcttgt gggtggtccg taatccaccc gagttagaaa agacagaact ggatttgaaa      960
tcactcttac cagaaggatt cttaagccga accgaagaca aagggatggt cgtgaaatca     1020
tgggctccgc aagttccggt tctgaatcat aaagcagtcg ggggattcgt cactcattgc     1080
ggttggaatt caattcttga agctgtttgt gctggtgtgc cgatggtggc ttggccgttg     1140
tacgctgagc agaggtttaa tagagtgatg attgtggatg agatcaagat tgcgatttcg     1200
atgaatgaat cagagacggg tttcgtgagc tctacagagg tggagaaacg agtccaagag     1260
ataattgggg agtgtccggt tagggagcga accatggcta tgaagaacgc agccgaatta     1320
gccttgacag aaactggttc gtctcatacc gcattaacta ctttactcca gtcgtggagc     1380
ccaaagtga                                                             1389
```

<210> SEQ ID NO 8
<211> LENGTH: 462
<212> TYPE: PRT
<213> ORGANISM: Arabidopsis thaliana

<400> SEQUENCE: 8

```
Met Gly Glu Glu Ala Ile Val Leu Tyr Pro Ala Pro Pro Ile Gly His
1               5                   10                  15

Leu Val Ser Met Val Glu Leu Gly Lys Thr Ile Leu Ser Lys Asn Pro
            20                  25                  30

Ser Leu Ser Ile His Ile Ile Leu Val Pro Pro Tyr Gln Pro Glu
        35                  40                  45

Ser Thr Ala Thr Tyr Ile Ser Ser Val Ser Ser Ser Phe Pro Ser Ile
    50                  55                  60

Thr Phe His His Leu Pro Ala Val Thr Pro Tyr Ser Ser Ser Thr
65                  70                  75                  80

Ser Arg His His His Glu Ser Leu Leu Leu Glu Ile Leu Cys Phe Ser
                85                  90                  95

Asn Pro Ser Val His Arg Thr Leu Phe Ser Leu Ser Arg Asn Phe Asn
            100                 105                 110

Val Arg Ala Met Ile Ile Asp Phe Phe Cys Thr Ala Val Leu Asp Ile
        115                 120                 125

Thr Ala Asp Phe Thr Phe Pro Val Tyr Phe Phe Tyr Thr Ser Gly Ala
    130                 135                 140

Ala Cys Leu Ala Phe Ser Phe Tyr Leu Pro Thr Ile Asp Glu Thr Thr
145                 150                 155                 160

Pro Gly Lys Asn Leu Lys Asp Ile Pro Thr Val His Ile Pro Gly Val
                165                 170                 175

Pro Pro Met Lys Gly Ser Asp Met Pro Lys Ala Val Leu Glu Arg Asp
            180                 185                 190

Asp Glu Val Tyr Asp Val Phe Ile Met Phe Gly Lys Gln Leu Ser Lys
        195                 200                 205

Ser Ser Gly Ile Ile Ile Asn Thr Phe Asp Ala Leu Glu Asn Arg Ala
    210                 215                 220

Ile Lys Ala Ile Thr Glu Glu Leu Cys Phe Arg Asn Ile Tyr Pro Ile
225                 230                 235                 240
```

```
Gly Pro Leu Ile Val Asn Gly Arg Ile Glu Asp Arg Asn Asp Asn Lys
                245                 250                 255

Ala Val Ser Cys Leu Asn Trp Leu Asp Ser Gln Pro Glu Lys Ser Val
            260                 265                 270

Val Phe Leu Cys Phe Gly Ser Leu Gly Leu Phe Ser Lys Glu Gln Val
        275                 280                 285

Ile Glu Ile Ala Val Gly Leu Glu Lys Ser Gly Gln Arg Phe Leu Trp
    290                 295                 300

Val Val Arg Asn Pro Pro Glu Leu Glu Lys Thr Glu Leu Asp Leu Lys
305                 310                 315                 320

Ser Leu Leu Pro Glu Gly Phe Leu Ser Arg Thr Glu Asp Lys Gly Met
                325                 330                 335

Val Val Lys Ser Trp Ala Pro Gln Val Pro Val Leu Asn His Lys Ala
            340                 345                 350

Val Gly Gly Phe Val Thr His Cys Gly Trp Asn Ser Ile Leu Glu Ala
        355                 360                 365

Val Cys Ala Gly Val Pro Met Val Ala Trp Pro Leu Tyr Ala Glu Gln
    370                 375                 380

Arg Phe Asn Arg Val Met Ile Val Asp Glu Ile Lys Ile Ala Ile Ser
385                 390                 395                 400

Met Asn Glu Ser Glu Thr Gly Phe Val Ser Ser Thr Glu Val Glu Lys
                405                 410                 415

Arg Val Gln Glu Ile Ile Gly Glu Cys Pro Val Arg Glu Arg Thr Met
            420                 425                 430

Ala Met Lys Asn Ala Ala Glu Leu Ala Leu Thr Glu Thr Gly Ser Ser
        435                 440                 445

His Thr Ala Leu Thr Thr Leu Leu Gln Ser Trp Ser Pro Lys
    450                 455                 460

<210> SEQ ID NO 9
<211> LENGTH: 1488
<212> TYPE: DNA
<213> ORGANISM: Arabidopsis thaliana

<400> SEQUENCE: 9
atggctttcg aaaaaaacaa cgaaccttt cctcttcact tgttctcttc cctttcatg     60 gctcaaggcc acatgattcc catggttgat attgcaaggc tcttggctca gcgaggtgtg    120
cttataacaa ttgtcacgac gcctcacaat gcagcaaggt tcaagaatgt cctaaaccgt    180
gccattgagt ctggtttgcc catcaaccta gtgcaagtca gtttccata tcaagaagct    240 ggtctgcaag aaggacaaga aaatatggat ttgcttacca cgatggagca gataacatct    300
ttctttaaag cggttaactt actcaaagaa ccagtccaga accttattga agagatgagc    360
ccgcgaccaa gctgtctaat ctctgatatg tgtttgtcgt atacaagcga aatcgccaag    420
aagttcaaaa taccaagat cctcttccat ggcatgggtt gcttttgtct tctgtgtgtt    480
aacgttctgc gcaagaaccg tgagatcttg acaatttaa agtctgataa ggagtacttc    540
attgttcctt attttcctga tagagttgaa ttcacaagac ctcaagttcc ggtggaaaca    600
tatgttcctg caggctggaa agagatcttg gaggatatgg tagaagcgga taagacatct    660
tatggtgtta tagtcaactc atttcaagag ctcgaacctg cgtatgccaa agacttcaag    720
gaggcaaggt ctggtaaagc atggaccatt ggacctgttt ccttgtgcaa caaggtagga    780
gtagacaaag cagagagggg aaacaaatca gatattgatc aagatgagtg ccttgaatgg    840
```

```
ctcgattcta aggaaccggg atctgtgctc tacgtttgcc ttggaagtat ttgtaatctt    900
cctctgtctc agctccttga gctgggacta ggcctagagg aatcccaaag acctttcatc    960
tgggtcataa gaggttggga gaaatacaaa gagttagttg agtggttctc ggaaagcggc   1020
tttgaagata gaatccaaga taggactt ctcatcaaag gatggtcccc tcaaatgctt     1080
atcctttcac atccttctgt tggagggttc ttaacgcact gcggatggaa ctcgactctt   1140 gagggataa ctgctggtct accaatgctt acatggccac tatttgcaga ccaattctgc    1200
aacgagaaac tggtcgtaca aatactaaaa gtcggtgtaa gtgccgaggt taaagaggtc   1260
atgaaatggg gagaagaaga gaagatagga gtgttggtgg ataaagaagg agtgaagaag   1320
gcagtggaag aactaatggg tgagagtgat gatgcaaaag agaagaag aagagccaaa     1380 gagcttggag aatcagctca caaggctgtg gaagaaggag ctcctctca ttctaatatc    1440 actttcttgc tacaagacat aatgcaacta gcacagtcca ataattga                1488
```

```
<210> SEQ ID NO 10
<211> LENGTH: 495
<212> TYPE: PRT
<213> ORGANISM: Arabidopsis thaliana

<400> SEQUENCE: 10

Met Ala Phe Glu Lys Asn Asn Glu Pro Phe Pro Leu His Phe Val Leu
1               5                   10                  15

Phe Pro Phe Met Ala Gln Gly His Met Ile Pro Met Val Asp Ile Ala
                20                  25                  30

Arg Leu Leu Ala Gln Arg Gly Val Leu Ile Thr Ile Val Thr Thr Pro
            35                  40                  45

His Asn Ala Ala Arg Phe Lys Asn Val Leu Asn Arg Ala Ile Glu Ser
        50                  55                  60

Gly Leu Pro Ile Asn Leu Val Gln Val Lys Phe Pro Tyr Gln Glu Ala
65                  70                  75                  80

Gly Leu Gln Glu Gly Gln Glu Asn Met Asp Leu Leu Thr Thr Met Glu
                85                  90                  95

Gln Ile Thr Ser Phe Phe Lys Ala Val Asn Leu Leu Lys Glu Pro Val
                100                 105                 110

Gln Asn Leu Ile Glu Glu Met Ser Pro Arg Pro Ser Cys Leu Ile Ser
            115                 120                 125

Asp Met Cys Leu Ser Tyr Thr Ser Glu Ile Ala Lys Lys Phe Lys Ile
        130                 135                 140

Pro Lys Ile Leu Phe His Gly Met Gly Cys Phe Cys Leu Leu Cys Val
145                 150                 155                 160

Asn Val Leu Arg Lys Asn Arg Glu Ile Leu Asp Asn Leu Lys Ser Asp
                165                 170                 175

Lys Glu Tyr Phe Ile Val Pro Tyr Phe Pro Asp Arg Val Glu Phe Thr
                180                 185                 190

Arg Pro Gln Val Pro Val Glu Thr Tyr Val Pro Ala Gly Trp Lys Glu
            195                 200                 205

Ile Leu Glu Asp Met Val Glu Ala Asp Lys Thr Ser Tyr Gly Val Ile
        210                 215                 220

Val Asn Ser Phe Gln Glu Leu Glu Pro Ala Tyr Ala Lys Asp Phe Lys
225                 230                 235                 240

Glu Ala Arg Ser Gly Lys Ala Trp Thr Ile Gly Pro Val Ser Leu Cys
                245                 250                 255

Asn Lys Val Gly Val Asp Lys Ala Glu Arg Gly Asn Lys Ser Asp Ile
```

```
                260                 265                 270
Asp Gln Asp Glu Cys Leu Glu Trp Leu Asp Ser Lys Glu Pro Gly Ser
            275                 280                 285
Val Leu Tyr Val Cys Leu Gly Ser Ile Cys Asn Leu Pro Leu Ser Gln
            290                 295                 300
Leu Leu Glu Leu Gly Leu Gly Leu Glu Glu Ser Gln Arg Pro Phe Ile
305                 310                 315                 320
Trp Val Ile Arg Gly Trp Glu Lys Tyr Lys Glu Leu Val Glu Trp Phe
                325                 330                 335
Ser Glu Ser Gly Phe Glu Asp Arg Ile Gln Asp Arg Gly Leu Leu Ile
            340                 345                 350
Lys Gly Trp Ser Pro Gln Met Leu Ile Leu Ser His Pro Ser Val Gly
            355                 360                 365
Gly Phe Leu Thr His Cys Gly Trp Asn Ser Thr Leu Glu Gly Ile Thr
            370                 375                 380
Ala Gly Leu Pro Met Leu Thr Trp Pro Leu Phe Ala Asp Gln Phe Cys
385                 390                 395                 400
Asn Glu Lys Leu Val Val Gln Ile Leu Lys Val Gly Val Ser Ala Glu
            405                 410                 415
Val Lys Glu Val Met Lys Trp Gly Glu Glu Lys Ile Gly Val Leu
            420                 425                 430
Val Asp Lys Glu Gly Val Lys Lys Ala Val Glu Leu Met Gly Glu
            435                 440                 445
Ser Asp Asp Ala Lys Glu Arg Arg Arg Ala Lys Glu Leu Gly Glu
            450                 455                 460
Ser Ala His Lys Ala Val Glu Glu Gly Gly Ser His Ser Asn Ile
465                 470                 475                 480
Thr Phe Leu Leu Gln Asp Ile Met Gln Leu Ala Gln Ser Asn Asn
                485                 490                 495

<210> SEQ ID NO 11
<211> LENGTH: 1488
<212> TYPE: DNA
<213> ORGANISM: Arabidopsis thaliana

<400> SEQUENCE: 11
atggtttccg aaacaaccaa atcttctcca cttcactttg ttctcttccc tttcatggct      60
caaggccaca tgattcccat ggttgatatt gcaaggctct ggctcagcg tggtgtgatc     120 ataacaattg tcacgacgcc tcacaatgca gcgaggttca gaatgtcct aaaccgtgcc     180 attgagtctg gcttgcccat caacttagtg caagtcaagt ttccatatct agaagctggt     240
ttgcaagaag acaagagaa tatcgattct cttgacacaa tggagcggat gatacctttc     300
tttaaagcgg ttaactttct cgaagaacca gtccagaagc tcattgaaga gatgaaccct     360
cgaccaagct gtctaatttc tgatttttgt ttgccttata caagcaaaat cgccaagaag     420
ttcaatatcc caaagatcct cttccatggc atgggttgct tttgtcttct gtgtatgcat     480
gttttacgca agaaccgtga gatcttggac aatttaaagt cagataagga cttttcact     540 gttcctgatt ttcctgatag agttgaattc acaagaacgc aagttccggt agaaacatat     600
gttccagctg agactggaaa agatatcttt gatggtatgg tagaagcgaa tgagacatct     660
tatggtgtga tcgtcaactc atttcaagag ctcgagcctg cttatgccaa agactacaag     720
gaggtaaggt ccggtaaagc atggaccatt ggacccgttt ccttgtgcaa caaggtagga     780
gccgacaaag cagagagggg aaacaaatca gacattgatc aagatgagtg ccttaaatgg     840
```

```
ctcgattcta agaaacatgg ctcggtgctt tacgtttgtc ttggaagtat ctgtaatctt    900
cctttgtctc aactcaagga gctgggacta ggcctagagg aatcccaaag acctttcatt    960
tgggtcataa gaggttggga gaagtacaaa gagttagttg agtggttctc ggaaagcggc   1020
tttgaagata gaatccaaga tagaggactt ctcatcaaag gatggtcccc tcaaatgctt   1080
atcctttcac atccatcagt tggagggttc ctaacacact gtggttggaa ctcgactctt   1140
gagggtataa ctgctggtct accgctactt acatggccgc tattcgcaga ccaattctgc   1200
aatgagaaat tggtcgttga ggtactaaaa gccggtgtaa gatccggggt tgaacagcct   1260
atgaaatggg gagaagagga gaaaatagga gtgttggtgg ataagaagg agtgaagaag    1320 gcagtggaag aattaatggg tgagagtgat gatgcaaaag agaagaag aagagccaaa     1380 gagcttggag attcagctca caaggctgtg gaagaaggag gctcttctca ttctaacatc   1440
tctttcttgc tacaagacat aatggaactg gcagaaccca ataattga                1488
```

<210> SEQ ID NO 12
<211> LENGTH: 495
<212> TYPE: PRT
<213> ORGANISM: Arabidopsis thaliana
<400> SEQUENCE: 12

```
Met Val Ser Glu Thr Thr Lys Ser Ser Pro Leu His Phe Val Leu Phe
1               5                   10                  15

Pro Phe Met Ala Gln Gly His Met Ile Pro Met Val Asp Ile Ala Arg
            20                  25                  30

Leu Leu Ala Gln Arg Gly Val Ile Ile Thr Ile Val Thr Thr Pro His
        35                  40                  45

Asn Ala Ala Arg Phe Lys Asn Val Leu Asn Arg Ala Ile Glu Ser Gly
    50                  55                  60

Leu Pro Ile Asn Leu Val Gln Val Lys Phe Pro Tyr Leu Glu Ala Gly
65                  70                  75                  80

Leu Gln Glu Gly Gln Glu Asn Ile Asp Ser Leu Asp Thr Met Glu Arg
                85                  90                  95

Met Ile Pro Phe Phe Lys Ala Val Asn Phe Leu Glu Glu Pro Val Gln
            100                 105                 110

Lys Leu Ile Glu Glu Met Asn Pro Arg Pro Ser Cys Leu Ile Ser Asp
        115                 120                 125

Phe Cys Leu Pro Tyr Thr Ser Lys Ile Ala Lys Lys Phe Asn Ile Pro
    130                 135                 140

Lys Ile Leu Phe His Gly Met Gly Cys Phe Cys Leu Leu Cys Met His
145                 150                 155                 160

Val Leu Arg Lys Asn Arg Glu Ile Leu Asp Asn Leu Lys Ser Asp Lys
                165                 170                 175

Glu Leu Phe Thr Val Pro Asp Phe Pro Asp Arg Val Glu Phe Thr Arg
            180                 185                 190

Thr Gln Val Pro Val Glu Thr Tyr Val Pro Ala Gly Asp Trp Lys Asp
        195                 200                 205

Ile Phe Asp Gly Met Val Glu Ala Asn Glu Thr Ser Tyr Gly Val Ile
    210                 215                 220

Val Asn Ser Phe Gln Glu Leu Glu Pro Ala Tyr Ala Lys Asp Tyr Lys
225                 230                 235                 240

Glu Val Arg Ser Gly Lys Ala Trp Thr Ile Gly Pro Val Ser Leu Cys
                245                 250                 255
```

-continued

```
Asn Lys Val Gly Ala Asp Lys Ala Glu Arg Gly Asn Lys Ser Asp Ile
            260                 265                 270

Asp Gln Asp Glu Cys Leu Lys Trp Leu Asp Ser Lys Lys His Gly Ser
        275                 280                 285

Val Leu Tyr Val Cys Leu Gly Ser Ile Cys Asn Leu Pro Leu Ser Gln
    290                 295                 300

Leu Lys Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

Ala Gly Leu Pro Leu Leu Thr Trp Pro Leu Phe Ala Asp Gln Phe Cys
385                 390                 395                 400

Asn Glu Lys Leu Val Val Glu Val Leu Lys Ala Gly Val Arg Ser Gly
                405                 410                 415

Val Glu Gln Pro Met Lys Trp Gly Glu Glu Lys Ile Gly Val Leu
            420                 425                 430

Val Asp Lys Glu Gly Val Lys Lys Ala Val Glu Leu Met Gly Glu
        435                 440                 445

Ser Asp Asp Ala Lys Arg Arg Arg Arg Ala Lys Glu Leu Gly Asp
    450                 455                 460

Ser Ala His Lys Ala Val Glu Glu Gly Gly Ser Ser His Ser Asn Ile
465                 470                 475                 480

Ser Phe Leu Leu Gln Asp Ile Met Glu Leu Ala Glu Pro Asn Asn
                485                 490                 495

<210> SEQ ID NO 13
<211> LENGTH: 1476
<212> TYPE: DNA
<213> ORGANISM: Arabidopsis thaliana

<400> SEQUENCE: 13
atggcatcgg aatttcgtcc tcctcttcat tttgttctct tccctttcat ggctcaaggc      60
cacatgatcc aatggtaga tattgcaagg ctcctggctc agcgcggggt gactataacc     120
attgtcacta cacctcaaaa cgcaggccgg ttcaagaacg ttcttagccg ggctatccaa     180
tccggcttgc ccatcaatct cgtgcaagta aagtttccat ctcaagaatc gggttcaccg     240
gaaggacaga gaatttgga cttgctcgat tcattgggg cttcattaac cttcttcaaa      300
gcatttagcc tgctcgagga accagtcgag aagctcttga agagattca acctaggcca     360 aactgcataa tcgctgacat gtgtttgcct tatacaaaca gaattgccaa gaatcttggt     420
ataccaaaaa tcatctttca tggcatgtgt tgcttcaatc ttctttgtac gcacataatg     480 caccaaaaacc acgagttctt ggaaactata gagtctgaca aggaatactt cccccattcct     540 aatttccctg acagagttga gttcacaaaa tctcagcttc caatggtatt agttgctgga     600
gattggaaag acttccttga cggaatgaca gaaggggata cacttcctta tggtgtgatt     660
gttaacacgt ttgaagagct cgagccagct tatgttagag actacaagaa ggttaaagcg     720
ggtaagatat ggagcatcgg accggtttcc ttgtgcaaca agttaggaga gaccaagct     780
```

-continued

```
gagagggggaa acaaggcgga cattgatcaa gacgagtgta ttaaatggct tgattctaaa    840
gaagaagggt cggtgctata tgtttgcctt ggaagtatat gcaatcttcc tctgtctcag    900
ctcaaagagc tcggcttagg cctcgaggaa tcccaaagac ctttcatttg ggtcataaga    960
ggttgggaga agtataacga gttacttgaa tggatctcag agagcggtta taaggaaaga   1020
atcaaagaaa gaggccttct cataacagga tggtcgcctc aaatgcttat ccttacacat   1080
cctgccgttg gaggattctt gacacattgt ggatggaact ctactcttga aggaatcact   1140
tcaggcgttc cattactcac gtggccactg tttggagacc aattctgcaa tgagaaattg   1200
gcggtgcaga tactaaaagc cggtgtgaga gctggggttg aagagtccat gagatgggga   1260
gaagaggaga aaataggagt actggtggat aaagaaggag taaagaaggc agtggaggaa   1320
ttgatgggtg atagtaatga tgctaaggag agaagaaaaa gagtgaaaga gcttggagaa   1380
ttagctcaca aggctgtgga agaaggaggc tcttctcatt ccaacatcac attcttgcta   1440
caagacataa tgcaattaga acaacccaag aaatga                            1476
```

<210> SEQ ID NO 14
<211> LENGTH: 491
<212> TYPE: PRT
<213> ORGANISM: Arabidopsis thaliana

<400> SEQUENCE: 14

Met Ala Ser Glu Phe Arg Pro Pro Leu His Phe Val Leu Phe Pro Phe
1               5                   10                  15

Met Ala Gln Gly His Met Ile Pro Met Val Asp Ile Ala Arg Leu Leu
                20                  25                  30

Ala Gln Arg Gly Val Thr Ile Thr Ile Val Thr Thr Pro Gln Asn Ala
            35                  40                  45

Gly Arg Phe Lys Asn Val Leu Ser Arg Ala Ile Gln Ser Gly Leu Pro
        50                  55                  60

Ile Asn Leu Val Gln Val Lys Phe Pro Ser Gln Glu Ser Gly Ser Pro
65                  70                  75                  80

Glu Gly Gln Glu Asn Leu Asp Leu Leu Asp Ser Leu Gly Ala Ser Leu
                85                  90                  95

Thr Phe Phe Lys Ala Phe Ser Leu Leu Glu Glu Pro Val Glu Lys Leu
            100                 105                 110

Leu Lys Glu Ile Gln Pro Arg Pro Asn Cys Ile Ala Asp Met Cys
        115                 120                 125

Leu Pro Tyr Thr Asn Arg Ile Ala Lys Asn Leu Gly Ile Pro Lys Ile
130                 135                 140

Ile Phe His Gly Met Cys Cys Phe Asn Leu Leu Cys Thr His Ile Met
145                 150                 155                 160

His Gln Asn His Glu Phe Leu Glu Thr Ile Glu Ser Asp Lys Glu Tyr
                165                 170                 175

Phe Pro Ile Pro Asn Phe Pro Asp Arg Val Glu Phe Thr Lys Ser Gln
            180                 185                 190

Leu Pro Met Val Leu Val Ala Gly Asp Trp Lys Asp Phe Leu Asp Gly
        195                 200                 205

Met Thr Glu Gly Asp Asn Thr Ser Tyr Gly Val Ile Val Asn Thr Phe
    210                 215                 220

Glu Glu Leu Glu Pro Ala Tyr Val Arg Asp Tyr Lys Lys Val Lys Ala
225                 230                 235                 240

Gly Lys Ile Trp Ser Ile Gly Pro Val Ser Leu Cys Asn Lys Leu Gly
                245                 250                 255

```
Glu Asp Gln Ala Glu Arg Gly Asn Lys Ala Asp Ile Asp Gln Asp Glu
            260                 265                 270
Cys Ile Lys Trp Leu Asp Ser Lys Glu Glu Gly Ser Val Leu Tyr Val
        275                 280                 285
Cys Leu Gly Ser Ile Cys Asn Leu Pro Leu Ser Gln Leu Lys Glu Leu
    290                 295                 300
Gly Leu Gly Leu Glu Glu Ser Gln Arg Pro Phe Ile Trp Val Ile Arg
305                 310                 315                 320
Gly Trp Glu Lys Tyr Asn Glu Leu Leu Glu Trp Ile Ser Glu Ser Gly
                325                 330                 335
Tyr Lys Glu Arg Ile Lys Glu Arg Gly Leu Leu Ile Thr Gly Trp Ser
            340                 345                 350
Pro Gln Met Leu Ile Leu Thr His Pro Ala Val Gly Gly Phe Leu Thr
        355                 360                 365
His Cys Gly Trp Asn Ser Thr Leu Glu Gly Ile Thr Ser Gly Val Pro
    370                 375                 380
Leu Leu Thr Trp Pro Leu Phe Gly Asp Gln Phe Cys Asn Glu Lys Leu
385                 390                 395                 400
Ala Val Gln Ile Leu Lys Ala Gly Val Arg Ala Gly Val Glu Glu Ser
                405                 410                 415
Met Arg Trp Gly Glu Glu Glu Lys Ile Gly Val Leu Val Asp Lys Glu
            420                 425                 430
Gly Val Lys Lys Ala Val Glu Glu Leu Met Gly Asp Ser Asn Asp Ala
        435                 440                 445
Lys Glu Arg Arg Lys Arg Val Lys Leu Gly Leu Ala His Lys
    450                 455                 460
Ala Val Glu Glu Gly Gly Ser Ser His Ser Asn Ile Thr Phe Leu Leu
465                 470                 475                 480
Gln Asp Ile Met Gln Leu Glu Gln Pro Lys Lys
                485                 490

<210> SEQ ID NO 15
<211> LENGTH: 1362
<212> TYPE: DNA
<213> ORGANISM: Arabidopsis thaliana

<400> SEQUENCE: 15
atggaagaac taggagtgaa gagaaggata gtattggttc cagttccagc acaaggtcat      60
gtaactccga ttatgcaact cgggaaggct ctttactcca agggcttctc catcactgtt     120
gttctcacac agtataatcg agttagctca tccaaggact tctctgattt tcatttcctc     180
accatcccag gcagcttgac cgagtctgat ctcaaaaacc ttggaccatt caagtttctc     240
ttcaagctca atcaaatttg cgaggcaagc ttcaagcaat gtattggtca actattgcag     300
gagcaaggta atgatatcgc ttgtgtcgtc tacgatgagt acatgtactt ctcccaagct     360
gcagttaaag agtttcaact tcctagcgtc ctcttcagca cgacaagtgc tactgccttt     420
gtctgtcgct ctgttttgtc tagagtcaac gcagagtcat tcttgcttga catgaaagat     480
cccaaagtgt cagacaagga atttccaggg ttgcatccgc taaggtacaa ggacctgcca     540
acttcagcat ttgggccatt agagagtata ctcaaggttt acagtgagac tgtcaacatt     600
cgaacagctt cggcagttat catcaactca acaagctgtc tagagagctc atctttggca     660
tggttacaaa acaactgca agttccagtg tatcctatag gcccacttca cattgcagct     720
tcagcgcctt ctagtttact tgaagaggac aggagttgcc ttgagtggtt gaacaagcaa     780
```

-continued

```
aaaataggct cagtgattta cataagtttg ggaagcttgg ctctaatgga aactaaagac    840
atgttggaga tggcttgggg tttacgtaat agcaaccaac ctttcttatg ggtgatccga    900
ccgggttcta ttcccggctc ggaatggaca gagtctttac cggaggaatt cagtaggttg    960
gtttcagaaa gaggttacat tgtgaaatgg caccacaga tagaagttct cagacatcct   1020
gcagtgggag ggttttggag tcactgcgga tggaactcga ccctagagag catcggggaa   1080
ggagttccga tgatctgtag gccttttacg ggagatcaga aagtcaatgc gaggtactta   1140
gagagagttt ggagaattgg ggttcaattg gaaggagagc tggataaagg aacagtggag   1200
agagctgtag agagattgat tatggatgaa gaaggagcag aaatgaggaa gagagttatc   1260
aacttgaaag agaagcttca agcctctgtc aagagtagag gttcctcatt cagctcatta   1320
gacaactttg tcaattcctt aaaaatgatg aatttcatgt ag                      1362
```

<210> SEQ ID NO 16
<211> LENGTH: 453
<212> TYPE: PRT
<213> ORGANISM: Arabidopsis thaliana

<400> SEQUENCE: 16

```
Met Glu Glu Leu Gly Val Lys Arg Arg Ile Val Leu Val Pro Val Pro
1               5                   10                  15

Ala Gln Gly His Val Thr Pro Ile Met Gln Leu Gly Lys Ala Leu Tyr
            20                  25                  30

Ser Lys Gly Phe Ser Ile Thr Val Val Leu Thr Gln Tyr Asn Arg Val
        35                  40                  45

Ser Ser Ser Lys Asp Phe Ser Asp Phe His Phe Leu Thr Ile Pro Gly
    50                  55                  60

Ser Leu Thr Glu Ser Asp Leu Lys Asn Leu Gly Pro Phe Lys Phe Leu
65                  70                  75                  80

Phe Lys Leu Asn Gln Ile Cys Glu Ala Ser Phe Lys Gln Cys Ile Gly
                85                  90                  95

Gln Leu Leu Gln Glu Gln Gly Asn Asp Ile Ala Cys Val Val Tyr Asp
            100                 105                 110

Glu Tyr Met Tyr Phe Ser Gln Ala Ala Val Lys Glu Phe Gln Leu Pro
        115                 120                 125

Ser Val Leu Phe Ser Thr Thr Ser Ala Thr Ala Phe Val Cys Arg Ser
    130                 135                 140

Val Leu Ser Arg Val Asn Ala Glu Ser Phe Leu Leu Asp Met Lys Asp
145                 150                 155                 160

Pro Lys Val Ser Asp Lys Glu Phe Pro Gly Leu His Pro Leu Arg Tyr
                165                 170                 175

Lys Asp Leu Pro Thr Ser Ala Phe Gly Pro Leu Glu Ser Ile Leu Lys
            180                 185                 190

Val Tyr Ser Glu Thr Val Asn Ile Arg Thr Ala Ser Ala Val Ile Ile
        195                 200                 205

Asn Ser Thr Ser Cys Leu Glu Ser Ser Leu Ala Trp Leu Gln Lys
    210                 215                 220

Gln Leu Gln Val Pro Val Tyr Pro Ile Gly Pro Leu His Ile Ala Ala
225                 230                 235                 240

Ser Ala Pro Ser Ser Leu Leu Glu Glu Asp Arg Ser Cys Leu Glu Trp
                245                 250                 255

Leu Asn Lys Gln Lys Ile Gly Ser Val Ile Tyr Ile Ser Leu Gly Ser
            260                 265                 270
```

```
Leu Ala Leu Met Glu Thr Lys Asp Met Leu Glu Met Ala Trp Gly Leu
            275                 280                 285

Arg Asn Ser Asn Gln Pro Phe Leu Trp Val Ile Arg Pro Gly Ser Ile
        290                 295                 300

Pro Gly Ser Glu Trp Thr Glu Ser Leu Pro Glu Glu Phe Ser Arg Leu
305                 310                 315                 320

Val Ser Glu Arg Gly Tyr Ile Val Lys Trp Ala Pro Gln Ile Glu Val
                325                 330                 335

Leu Arg His Pro Ala Val Gly Gly Phe Trp Ser His Cys Gly Trp Asn
            340                 345                 350

Ser Thr Leu Glu Ser Ile Gly Glu Gly Val Pro Met Ile Cys Arg Pro
        355                 360                 365

Phe Thr Gly Asp Gln Lys Val Asn Ala Arg Tyr Leu Glu Arg Val Trp
370                 375                 380

Arg Ile Gly Val Gln Leu Glu Gly Glu Leu Asp Lys Gly Thr Val Glu
385                 390                 395                 400

Arg Ala Val Glu Arg Leu Ile Met Asp Glu Glu Gly Ala Glu Met Arg
                405                 410                 415

Lys Arg Val Ile Asn Leu Lys Glu Lys Leu Gln Ala Ser Val Lys Ser
            420                 425                 430

Arg Gly Ser Ser Phe Ser Ser Leu Asp Asn Phe Val Asn Ser Leu Lys
        435                 440                 445

Met Met Asn Phe Met
    450

<210> SEQ ID NO 17
<211> LENGTH: 1446
<212> TYPE: DNA
<213> ORGANISM: Arabidopsis thaliana

<400> SEQUENCE: 17
atgagtagtg atcctcatcg taagctccat gttgtgttct tccctttcat ggcttatggt      60
cacatgatac caactctaga catggctaag cttttctcta gcagaggagc caaatctaca     120
atcctcacca cacctctcaa ctccaagatc ttccaaaaac ccatcgaaag attcaagaac     180
ctgaatccga gtttcgaaat cgacatccag atcttcgatt tcccttgcgt ggatctcggg     240
ttaccagaag gatgcgaaaa cgtcgatttc ttcacctcaa caacaatga tgatagacag     300 tatctgacct tgaagttctt taagtcgaca aggttttttca aagatcagct tgagaagctc     360
ctcgagacaa cgagaccaga ctgtcttatc gccgacatgt tcttcccctg gctacggaa     420 gctgctgaga agttcaatgt gccaagactt gtgttccacg gtactggcta cttttcttta     480
tgctctgaat attgcatcag agtgcataac ccacaaaaca tagtagcttc aaggtacgag     540
ccatttgtga ttcctgatct cccggggaac atagtgataa ctcaagaaca gatagcagac     600
cgtgacgaag aaagcgagat ggggaagttt atgattgagg tcaaagaatc tgatgtgaag     660
agctcaggtg ttattgtaaa cagcttctac gagcttgaac ctgattacgc cgactttac     720 aagagtgttg tactgaagag agcgtggcat atcggtccgc tttcggttta caacagagga     780
tttgaggaga aggctgagag aggaaagaaa gcaagcatta tgaggttga atgcctcaaa     840 tggcttgact ccaagaaacc agattcagtc atttacattt cttttgggag cgtggcttgc     900
ttcaagaacg agcagctatt cgagatcgct gcaggattag aaacttctgg agcaaatttc     960
atctgggttg ttaggaaaaa cataggtatt gaaaagaag aatggttacc agaagggttc    1020
```

-continued

```
gaagagaggg tgaaaggaaa agggatgatt ataagaggat gggcaccaca ggtgctcata    1080
cttgatcatc aagcaacttg tgggtttgtg acccattgcg gctggaactc gcttctggaa    1140
ggagtggctg cagggctacc aatggtgaca tggcctgtag cagcggagca attctacaat    1200
gagaaattgg ttacgcaagt gctcagaaca ggagtgagcg tgggagcgaa aaagaatgta    1260
agaactacgg gagatttcat tagcagagag aaagtggtta aagcggtgag ggaggtgttg    1320
gttggggaag aggcggatga gaggcgggag agggcaaaga agttggcaga gatggctaaa    1380
gctgccgtgg aaggagggtc ttctttcaac gatctaaaca gcttcataga agagtttacc    1440
tcgtaa    1446
```

```
<210> SEQ ID NO 18
<211> LENGTH: 481
<212> TYPE: PRT
<213> ORGANISM: Arabidopsis thaliana

<400> SEQUENCE: 18
```

| | | | | | | | | | | | | | | | |
|---|---|---|---|---|---|---|---|---|---|---|---|---|---|---|---|
| Met | Ser | Ser | Asp | Pro | His | Arg | Lys | Leu | His | Val | Phe | Phe | Pro | Phe | |
| 1 | | | | 5 | | | | | 10 | | | | | 15 | |
| Met | Ala | Tyr | Gly | His | Met | Ile | Pro | Thr | Leu | Asp | Met | Ala | Lys | Leu | Phe |
| | | | 20 | | | | | 25 | | | | | 30 | | |
| Ser | Ser | Arg | Gly | Ala | Lys | Ser | Thr | Ile | Leu | Thr | Thr | Pro | Leu | Asn | Ser |
| | | 35 | | | | | 40 | | | | | 45 | | | |
| Lys | Ile | Phe | Gln | Lys | Pro | Ile | Glu | Arg | Phe | Lys | Asn | Leu | Asn | Pro | Ser |
| | 50 | | | | | 55 | | | | | 60 | | | | |
| Phe | Glu | Ile | Asp | Ile | Gln | Ile | Phe | Asp | Phe | Pro | Cys | Val | Asp | Leu | Gly |
| 65 | | | | | 70 | | | | | 75 | | | | | 80 |
| Leu | Pro | Glu | Gly | Cys | Glu | Asn | Val | Asp | Phe | Phe | Thr | Ser | Asn | Asn | Asn |
| | | | | 85 | | | | | 90 | | | | | 95 | |
| Asp | Asp | Arg | Gln | Tyr | Leu | Thr | Leu | Lys | Phe | Phe | Lys | Ser | Thr | Arg | Phe |
| | | | 100 | | | | | 105 | | | | | 110 | | |
| Phe | Lys | Asp | Gln | Leu | Glu | Lys | Leu | Leu | Glu | Thr | Thr | Arg | Pro | Asp | Cys |
| | | 115 | | | | | 120 | | | | | 125 | | | |
| Leu | Ile | Ala | Asp | Met | Phe | Phe | Pro | Trp | Ala | Thr | Glu | Ala | Ala | Glu | Lys |
| | 130 | | | | | 135 | | | | | 140 | | | | |
| Phe | Asn | Val | Pro | Arg | Leu | Val | Phe | His | Gly | Thr | Gly | Tyr | Phe | Ser | Leu |
| 145 | | | | | 150 | | | | | 155 | | | | | 160 |
| Cys | Ser | Glu | Tyr | Cys | Ile | Arg | Val | His | Asn | Pro | Gln | Asn | Ile | Val | Ala |
| | | | | 165 | | | | | 170 | | | | | 175 | |
| Ser | Arg | Tyr | Glu | Pro | Phe | Val | Ile | Pro | Asp | Leu | Pro | Gly | Asn | Ile | Val |
| | | | 180 | | | | | 185 | | | | | 190 | | |
| Ile | Thr | Gln | Glu | Gln | Ile | Ala | Asp | Arg | Asp | Glu | Glu | Ser | Glu | Met | Gly |
| | | 195 | | | | | 200 | | | | | 205 | | | |
| Lys | Phe | Met | Ile | Glu | Val | Lys | Glu | Ser | Asp | Val | Lys | Ser | Ser | Gly | Val |
| | 210 | | | | | 215 | | | | | 220 | | | | |
| Ile | Val | Asn | Ser | Phe | Tyr | Glu | Leu | Glu | Pro | Asp | Tyr | Ala | Asp | Phe | Tyr |
| 225 | | | | | 230 | | | | | 235 | | | | | 240 |
| Lys | Ser | Val | Val | Leu | Lys | Arg | Ala | Trp | His | Ile | Gly | Pro | Leu | Ser | Val |
| | | | | 245 | | | | | 250 | | | | | 255 | |
| Tyr | Asn | Arg | Gly | Phe | Glu | Glu | Lys | Ala | Glu | Arg | Gly | Lys | Lys | Ala | Ser |
| | | | 260 | | | | | 265 | | | | | 270 | | |
| Ile | Asn | Glu | Val | Glu | Cys | Leu | Lys | Trp | Leu | Asp | Ser | Lys | Lys | Pro | Asp |
| | | 275 | | | | | 280 | | | | | 285 | | | |
| Ser | Val | Ile | Tyr | Ile | Ser | Phe | Gly | Ser | Val | Ala | Cys | Phe | Lys | Asn | Glu |

```
                  290                 295                 300

Gln Leu Phe Glu Ile Ala Ala Gly Leu Glu Thr Ser Gly Ala Asn Phe
305                 310                 315                 320

Ile Trp Val Val Arg Lys Asn Ile Gly Ile Glu Lys Glu Glu Trp Leu
                325                 330                 335

Pro Glu Gly Phe Glu Glu Arg Val Lys Gly Lys Gly Met Ile Ile Arg
            340                 345                 350

Gly Trp Ala Pro Gln Val Leu Ile Leu Asp His Gln Ala Thr Cys Gly
        355                 360                 365

Phe Val Thr His Cys Gly Trp Asn Ser Leu Leu Glu Gly Val Ala Ala
    370                 375                 380

Gly Leu Pro Met Val Thr Trp Pro Val Ala Ala Glu Gln Phe Tyr Asn
385                 390                 395                 400

Glu Lys Leu Val Thr Gln Val Leu Arg Thr Gly Val Ser Val Gly Ala
                405                 410                 415

Lys Lys Asn Val Arg Thr Thr Gly Asp Phe Ile Ser Arg Glu Lys Val
            420                 425                 430

Val Lys Ala Val Arg Glu Val Leu Val Gly Glu Glu Ala Asp Glu Arg
        435                 440                 445

Arg Glu Arg Ala Lys Lys Leu Ala Glu Met Ala Lys Ala Ala Val Glu
    450                 455                 460

Gly Gly Ser Ser Phe Asn Asp Leu Asn Ser Phe Ile Glu Glu Phe Thr
465                 470                 475                 480

Ser
```

<210> SEQ ID NO 19
<211> LENGTH: 1383
<212> TYPE: DNA
<213> ORGANISM: Arabidopsis thaliana

<400> SEQUENCE: 19

```
atggccaagc ttttcgctag aagaggagcc aaatcaactc tcctcacaac cccaataaat      60
gctaagatct ggagaaaacc cattgaagca ttcaaagttc aaaatcctga tctcgaaatc     120
ggaatcaaga tcctcaattt cccttgtgta gagcttggat tgccagaagg atgcgagaac     180
cgtgacttca ttaactcata ccaaaaatct gactcatttg acttgttctt gaagtttctt     240
ttctctacca agtatatgaa acagcagttg gagagtttca ttgaaacaac caaaccgagt     300
gctcttgtag ccgatatgtt cttcccttgg gcaacagaat ccgcggagaa gatcggtgtt     360
ccaagacttg tgttccacgg cacatcatcc tttgccttgt gttgttcgta taacatgagg     420
attcataagc cacacaagaa agtcgcttcg agttctactc catttgtaat ccctggtctc     480
cctggagaca tagttattac agaagaccaa gccaatgtca ccaacgaaga aactccattc     540
ggaaagtttt ggaaagaagt cagggaatca gagaccagta gctttggtgt tttggtgaat     600
agcttctacg agctggaatc atcttatgct gatttttacc gtagttttgt ggcgaaaaaa     660
gcgtggcata taggtccact ttcactatcc aacagaggga ttgcagagaa agccggaaga     720
gggaaaaagg caaacattga tgagcaagaa tgcctcaaat ggcttgactc taagacacct     780
ggctcagtag tttacttgtc ctttggtagc ggaaccggct acccaacga acagctgtta      840 gagattgctt tcggccttga aggctctgga caaaatttca tttgggtggt tagcaaaaat     900
gaaaaccaag ttgggacagg tgaaaatgaa gattggttgc ctaaagggtt tgaagagagg     960
aataaaggaa aagggctgat aatacgcgga tgggccccgc aagtgctgat acttgaccac    1020
```

```
aaagcaatcg gaggatttgt gacgcattgc ggatggaact cgactttgga gggcattgcc   1080
gcagggctgc ctatggtgac ttggccgatg ggggcagaac agttctacaa cgagaagtta   1140
ttgacaaaag tgttgagaat aggagtgaac gttggagcta ccgagttggt gaaaaaagga   1200
aagttgatta gtagagcaca agtggagaag gcagtaaggg aagtgattgg tggtgagaag   1260
gcagaggaaa ggcggctaag ggctaaggag ctgggcgaga tggctaaagc cgctgtggaa   1320
gaaggagggt cttcttataa tgatgtgaac aagtttatgg aagagctgaa tggtagaaag   1380
tag                                                                 1383
```

<210> SEQ ID NO 20
<211> LENGTH: 460
<212> TYPE: PRT
<213> ORGANISM: Arabidopsis thaliana

<400> SEQUENCE: 20

```
Met Ala Lys Leu Phe Ala Arg Arg Gly Ala Lys Ser Thr Leu Leu Thr
1               5                   10                  15

Thr Pro Ile Asn Ala Lys Ile Leu Glu Lys Pro Ile Glu Ala Phe Lys
            20                  25                  30

Val Gln Asn Pro Asp Leu Glu Ile Gly Ile Lys Ile Leu Asn Phe Pro
        35                  40                  45

Cys Val Glu Leu Gly Leu Pro Glu Gly Cys Glu Asn Arg Asp Phe Ile
    50                  55                  60

Asn Ser Tyr Gln Lys Ser Asp Ser Phe Asp Leu Phe Leu Lys Phe Leu
65                  70                  75                  80

Phe Ser Thr Lys Tyr Met Lys Gln Gln Leu Glu Ser Phe Ile Glu Thr
                85                  90                  95

Thr Lys Pro Ser Ala Leu Val Ala Asp Met Phe Phe Pro Trp Ala Thr
            100                 105                 110

Glu Ser Ala Glu Lys Ile Gly Val Pro Arg Leu Val Phe His Gly Thr
        115                 120                 125

Ser Ser Phe Ala Leu Cys Cys Ser Tyr Asn Met Arg Ile His Lys Pro
    130                 135                 140

His Lys Lys Val Ala Ser Ser Ser Thr Pro Phe Val Ile Pro Gly Leu
145                 150                 155                 160

Pro Gly Asp Ile Val Ile Thr Glu Asp Gln Ala Asn Val Thr Asn Glu
                165                 170                 175

Glu Thr Pro Phe Gly Lys Phe Trp Lys Glu Val Arg Glu Ser Glu Thr
            180                 185                 190

Ser Ser Phe Gly Val Leu Val Asn Ser Phe Tyr Glu Leu Glu Ser Ser
        195                 200                 205

Tyr Ala Asp Phe Tyr Arg Ser Phe Val Ala Lys Lys Ala Trp His Ile
    210                 215                 220

Gly Pro Leu Ser Leu Ser Asn Arg Gly Ile Ala Glu Lys Ala Gly Arg
225                 230                 235                 240

Gly Lys Lys Ala Asn Ile Asp Glu Gln Glu Cys Leu Lys Trp Leu Asp
                245                 250                 255

Ser Lys Thr Pro Gly Ser Val Val Tyr Leu Ser Phe Gly Ser Gly Thr
            260                 265                 270

Gly Leu Pro Asn Glu Gln Leu Leu Glu Ile Ala Phe Gly Leu Glu Gly
        275                 280                 285

Ser Gly Gln Asn Phe Ile Trp Val Val Ser Lys Asn Glu Asn Gln Val
    290                 295                 300
```

| | | | | | | | | | | | |
|---|---|---|---|---|---|---|---|---|---|---|---|
|Gly|Thr|Gly|Glu|Asn|Glu|Asp|Trp|Leu|Pro|Lys|Gly|Phe|Glu|Glu|Arg|
|305| | | |310| | | |315| | | |320| | | |
|Asn|Lys|Gly|Lys|Gly|Leu|Ile|Ile|Arg|Gly|Trp|Ala|Pro|Gln|Val|Leu|
| | | | |325| | | |330| | | |335| | | |
|Ile|Leu|Asp|His|Lys|Ala|Ile|Gly|Gly|Phe|Val|Thr|His|Cys|Gly|Trp|
| | | |340| | | |345| | | |350| | | | |
|Asn|Ser|Thr|Leu|Glu|Gly|Ile|Ala|Ala|Gly|Leu|Pro|Met|Val|Thr|Trp|
| | |355| | | |360| | | |365| | | | | |
|Pro|Met|Gly|Ala|Glu|Gln|Phe|Tyr|Asn|Glu|Lys|Leu|Leu|Thr|Lys|Val|
| |370| | | | |375| | | |380| | | | | |
|Leu|Arg|Ile|Gly|Val|Asn|Val|Gly|Ala|Thr|Glu|Leu|Val|Lys|Lys|Gly|
|385| | | |390| | | |395| | | |400| | | |
|Lys|Leu|Ile|Ser|Arg|Ala|Gln|Val|Glu|Lys|Ala|Val|Arg|Glu|Val|Ile|
| | | | |405| | | |410| | | |415| | | |
|Gly|Gly|Glu|Lys|Ala|Glu|Glu|Arg|Arg|Leu|Arg|Ala|Lys|Glu|Leu|Gly|
| | | |420| | | |425| | | |430| | | | |
|Glu|Met|Ala|Lys|Ala|Ala|Val|Glu|Glu|Gly|Gly|Ser|Ser|Tyr|Asn|Asp|
| | |435| | | |440| | | |445| | | | | |
|Val|Asn|Lys|Phe|Met|Glu|Glu|Leu|Asn|Gly|Arg|Lys| | | | |
|450| | | | |455| | | |460| | | | | | |

<210> SEQ ID NO 21
<211> LENGTH: 1540
<212> TYPE: DNA
<213> ORGANISM: Avena sativa

<400> SEQUENCE: 21

```
ctcgacacta aaacaaacgc accattgcca agagaaagat gggcgtcgcc acaatcagcg      60
cggtgccccg gaagctggcg gtgctctacc cgtcgccggg catgggccac attgtttcca     120
tgatcgagct cggcaagatc ttcgtcgccc gcggcctcgc cgtcaccatt gtcgtcatcg     180
acctgccgaa caacaccggc tcaagcgcaa cagggcccct cctcgcaggg gtctccgccg     240
ccaacccctc catctccttc accgactccc gcaggtgaag ctcccacacg tggagtcca      300
ggcacatcga aacgttgaac ttcgaggtcg cccgcgcggc gaacccacac ctgcgtgatt     360
tcctcgccgg aatatcgcct gacattttca tcgccgattt cttctgccat gtcgcccgcg     420
acgtggcatc ggagctcggt attcccttct acttcttctt cacctccggc gccgaggtcc     480
tggccgtcct tctgcatctc ccggtcctgc actctcagag caccgcaagc ttccaggaca     540
tgggtgagga gctcgtgcat gttcctggga ttccctcatt tccggcgtcg cactccatgc     600
tgccagtcat ggaccgtgac gacgcagcct acatggcatt cgtgaacgtg tgcagcgacc     660
tgtgccgctc ccagggcatc atcgtcaata ccttcagctc gttcgagccg cgggccatcg     720
aggccatcgc cgccgggctc tgtacaccgg ccggactccc gatccctgca ctccactgca     780
tcggcccgct gataaagtcg gaggaggtgg gcgtgaagcg cggcgacgag tgcatggcgt     840
ggctggacac gcagcccaag gacagcgtgg tgttcctctg cttcggcagc ctcggccggt     900
tcagcggcaa gcagatcagg gaggtggcgc tcgggctaga ggcaagcggg cagcggttcc     960
tctgggtcgt aaagagcccg cccaacgacg acccagcgaa gaagttcgag aatccttcgg    1020
agaagccgga cctcgacgcc ctcctcccgg agggattcct ggaccggacc aaggacaagg    1080
ggctggtcgt caagtcgtgg gcgccgcagc gcgacgtgct gatgcacgcc gcggtgggcg    1140
ggttcgtgac gcactgcggg tggaactcgg tgctggagtc cgtcatggcg ggcgtgccga    1200
tgctggcgtg gccgctgtac gcggagcagc gcatgaacaa ggtgttcctc gaggaggagc    1260
```

-continued

```
ttgggctagc cgtggcagtg aagggtatg acaaggaggt ggtggaggcc cgggaggtgg      1320
cagcgaaggt gaagtggatg atggactctg atggagggag ggtgatccgg gagcgcacgc      1380
aggcggcgat gcggcaggcg aagaagggga tgggcgaggg cggggagtcg gaggtgacat      1440
tggcgggact agtggacgcg tggacgacac atgcttgatg ttggtgggct cagttattat      1500
ttcgaaataa taactactcg taataaaaaa aaaaaaaaaa                            1540
```

<210> SEQ ID NO 22
<211> LENGTH: 479
<212> TYPE: PRT
<213> ORGANISM: Avena sativa

<400> SEQUENCE: 22

```
Met Gly Val Ala Thr Ile Ser Ala Val Pro Arg Lys Leu Ala Val Leu
1               5                   10                  15

Tyr Pro Ser Pro Gly Met Gly His Ile Val Ser Met Ile Glu Leu Gly
                20                  25                  30

Lys Ile Phe Val Ala Arg Gly Leu Ala Val Thr Ile Val Ile Asp
            35                  40                  45

Leu Pro Asn Asn Thr Gly Ser Ser Ala Thr Gly Pro Phe Leu Ala Gly
        50                  55                  60

Val Ser Ala Ala Asn Pro Ser Ile Ser Phe His Arg Leu Pro Gln Val
65                  70                  75                  80

Lys Leu Pro His Val Glu Ser Arg His Ile Glu Thr Leu Asn Phe Glu
                85                  90                  95

Val Ala Arg Ala Ala Asn Pro His Leu Arg Asp Phe Leu Ala Gly Ile
                100                 105                 110

Ser Pro Asp Ile Phe Ile Ala Asp Phe Phe Cys His Val Ala Arg Asp
            115                 120                 125

Val Ala Ser Glu Leu Gly Ile Pro Phe Tyr Phe Phe Thr Ser Gly
        130                 135                 140

Ala Glu Val Leu Ala Val Leu Leu His Leu Pro Val Leu His Ser Gln
145                 150                 155                 160

Ser Thr Ala Ser Phe Gln Asp Met Gly Glu Glu Leu Val His Val Pro
                165                 170                 175

Gly Ile Pro Ser Phe Pro Ala Ser His Ser Met Leu Pro Val Met Asp
            180                 185                 190

Arg Asp Asp Ala Ala Tyr Met Ala Phe Val Asn Val Cys Ser Asp Leu
        195                 200                 205

Cys Arg Ser Gln Gly Ile Ile Val Asn Thr Phe Ser Ser Phe Glu Pro
    210                 215                 220

Arg Ala Ile Glu Ala Ile Ala Ala Gly Leu Cys Thr Pro Ala Gly Leu
225                 230                 235                 240

Pro Ile Pro Ala Leu His Cys Ile Gly Pro Leu Ile Lys Ser Glu Glu
                245                 250                 255

Val Gly Val Lys Arg Gly Asp Glu Cys Met Ala Trp Leu Asp Thr Gln
            260                 265                 270

Pro Lys Asp Ser Val Val Phe Leu Cys Phe Gly Ser Leu Gly Arg Phe
        275                 280                 285

Ser Gly Lys Gln Ile Arg Glu Val Ala Leu Gly Leu Glu Ala Ser Gly
    290                 295                 300

Gln Arg Phe Leu Trp Val Val Lys Ser Pro Pro Asn Asp Pro Ala
305                 310                 315                 320
```

```
Lys Lys Phe Glu Asn Pro Ser Glu Lys Pro Asp Leu Asp Ala Leu Leu
            325                 330                 335

Pro Glu Gly Phe Leu Asp Arg Thr Lys Asp Lys Gly Leu Val Val Lys
        340                 345                 350

Ser Trp Ala Pro Gln Arg Asp Val Leu Met His Ala Ala Val Gly Gly
    355                 360                 365

Phe Val Thr His Cys Gly Trp Asn Ser Val Leu Glu Ser Val Met Ala
    370                 375                 380

Gly Val Pro Met Leu Ala Trp Pro Leu Tyr Ala Glu Gln Arg Met Asn
385                 390                 395                 400

Lys Val Phe Leu Glu Glu Glu Leu Gly Leu Ala Val Ala Val Glu Gly
                405                 410                 415

Tyr Asp Lys Glu Val Val Glu Ala Arg Glu Val Ala Ala Lys Val Lys
            420                 425                 430

Trp Met Met Asp Ser Asp Gly Gly Arg Val Ile Arg Glu Arg Thr Gln
        435                 440                 445

Ala Ala Met Arg Gln Ala Lys Lys Gly Met Gly Glu Gly Gly Glu Ser
    450                 455                 460

Glu Val Thr Leu Ala Gly Leu Val Asp Ala Trp Thr Thr His Ala
465                 470                 475
```

<210> SEQ ID NO 23
<211> LENGTH: 1359
<212> TYPE: DNA
<213> ORGANISM: Arabidopsis thaliana

<400> SEQUENCE: 23

```
atggagaaaa gggtagagaa gagaaggatt gtgttagttc cggttgctgc acaaggacat      60
gtaaccccaa tgatgcagct tgggaaagcc cttcaatcaa agggcttctt aattactgtt     120
gctcagagac agttcaatca aataggctca tcattgcaac actttcctgg ttttgacttt     180
gtcaccatac cagaaagctt acctcagtct gaatctaaga aactaggacc agctgagtat     240
cttatgaatc tcaacaaaac aagcgaggca agcttcaagg agtgtataag tcagttatcg     300
atgcaacaag gcaatgatat agcatgtatc atctatgaca agcttatgta cttctgtgaa     360
gcagcagcta aggagtttaa gattcctagt gttatcttca gcactagcag tgctacaatt     420
caagtttgct actgtgtttt aagtgaactc agtgccgaga agttcttgat cgacatgaaa     480
gatcctgaaa agcaagataa ggtgttggaa ggtttgcatc ctttaaggta caaagaccta     540
ccaacttcag gatttggacc attagagcca cttttggaga tgtgtaggga agtagttaac     600
aaaagaacag cttccgctgt tatcatcaac acggcgagct gtctagagag cttgtctctg     660
tcatggctgc aacaagaact tggaattcca gtgtatccat taggccctct tcacattaca     720
gcttcatcgc cgggacctag tttactgcaa gaggacatga gctgcattga atggctgaac     780
aagcagaaac caaggtcagt catatacata agcttgggaa ccaaagctca catggagacc     840
aaggagatgt tagagatggc ctggggattg ttgaatagca ccaaccttt cttatgggtc     900
atccgacctg gctctgttgc aggcttcgag tggatagagt tattaccaga ggaagtcatt     960
aagatggtaa cagaaagagg atacatagcg aaatgggcac cgcagataga agtacttgga    1020
catcctgcag tgggaggatt ctggagccac tgtggatgga actcaacact cgagagtatt    1080
gtggaaggag tcccaatgat tgcaggcct ttacaaggcg aacaaaagtt aaatgcgatg    1140
tatatagaaa gtgtttggaa atagggatt caacttgaag gtgaagtgga aagggaaggt    1200
gtagagagag ctgtgaagag gttgatcata gatgaagaag gtgcagccat gagggagagg    1260
```

```
gctcttgatt taaaagagaa gctcaatgcc tcggtaagaa gtggaggctc ctcatacaac    1320
gcactggatg agcttgtcaa gttcttgaat acagagtga                          1359
```

<210> SEQ ID NO 24
<211> LENGTH: 452
<212> TYPE: PRT
<213> ORGANISM: Arabidopsis thaliana

<400> SEQUENCE: 24

```
Met Glu Lys Arg Val Glu Lys Arg Arg Ile Val Leu Pro Val Ala
1               5                   10                  15

Ala Gln Gly His Val Thr Pro Met Met Gln Leu Gly Lys Ala Leu Gln
            20                  25                  30

Ser Lys Gly Phe Leu Ile Thr Val Ala Gln Arg Gln Phe Asn Gln Ile
        35                  40                  45

Gly Ser Ser Leu Gln His Phe Pro Gly Phe Asp Phe Val Thr Ile Pro
    50                  55                  60

Glu Ser Leu Pro Gln Ser Glu Ser Lys Lys Leu Gly Pro Ala Glu Tyr
65                  70                  75                  80

Leu Met Asn Leu Asn Lys Thr Ser Glu Ala Ser Phe Lys Glu Cys Ile
                85                  90                  95

Ser Gln Leu Ser Met Gln Gln Gly Asn Asp Ile Ala Cys Ile Ile Tyr
            100                 105                 110

Asp Lys Leu Met Tyr Phe Cys Glu Ala Ala Ala Lys Glu Phe Lys Ile
        115                 120                 125

Pro Ser Val Ile Phe Ser Thr Ser Ser Ala Thr Ile Gln Val Cys Tyr
    130                 135                 140

Cys Val Leu Ser Glu Leu Ser Ala Glu Lys Phe Leu Ile Asp Met Lys
145                 150                 155                 160

Asp Pro Glu Lys Gln Asp Lys Val Leu Glu Gly Leu His Pro Leu Arg
                165                 170                 175

Tyr Lys Asp Leu Pro Thr Ser Gly Phe Gly Pro Leu Glu Pro Leu Leu
            180                 185                 190

Glu Met Cys Arg Glu Val Val Asn Lys Arg Thr Ala Ser Ala Val Ile
        195                 200                 205

Ile Asn Thr Ala Ser Cys Leu Glu Ser Leu Ser Leu Ser Trp Leu Gln
    210                 215                 220

Gln Glu Leu Gly Ile Pro Val Tyr Pro Leu Gly Pro Leu His Ile Thr
225                 230                 235                 240

Ala Ser Ser Pro Gly Pro Ser Leu Leu Gln Glu Asp Met Ser Cys Ile
                245                 250                 255

Glu Trp Leu Asn Lys Gln Lys Pro Arg Ser Val Ile Tyr Ile Ser Leu
            260                 265                 270

Gly Thr Lys Ala His Met Glu Thr Lys Glu Met Leu Glu Met Ala Trp
        275                 280                 285

Gly Leu Leu Asn Ser Asn Gln Pro Phe Leu Trp Val Ile Arg Pro Gly
    290                 295                 300

Ser Val Ala Gly Phe Glu Trp Ile Glu Leu Leu Pro Glu Glu Val Ile
305                 310                 315                 320

Lys Met Val Thr Glu Arg Gly Tyr Ile Ala Lys Trp Ala Pro Gln Ile
                325                 330                 335

Glu Val Leu Gly His Pro Ala Val Gly Gly Phe Trp Ser His Cys Gly
            340                 345                 350
```

```
Trp Asn Ser Thr Leu Glu Ser Ile Val Glu Gly Val Pro Met Ile Cys
            355                 360                 365

Arg Pro Leu Gln Gly Glu Gln Lys Leu Asn Ala Met Tyr Ile Glu Ser
        370                 375                 380

Val Trp Lys Ile Gly Ile Gln Leu Glu Gly Glu Val Glu Arg Glu Gly
385                 390                 395                 400

Val Glu Arg Ala Val Lys Arg Leu Ile Ile Asp Glu Glu Gly Ala Ala
                405                 410                 415

Met Arg Glu Arg Ala Leu Asp Leu Lys Glu Lys Leu Asn Ala Ser Val
            420                 425                 430

Arg Ser Gly Gly Ser Ser Tyr Asn Ala Leu Asp Glu Leu Val Lys Phe
        435                 440                 445

Leu Asn Thr Glu
    450

<210> SEQ ID NO 25
<211> LENGTH: 2688
<212> TYPE: DNA
<213> ORGANISM: Arabidopsis thaliana

<400> SEQUENCE: 25
```

| | |
|---|---:|
| atggagaaaa gagtagagaa gagaaggata gtgttggttc cacttccatt actaggacat | 60 |
| ttcactccga tgatgcaact cggccaagcc cttatcttga agggattctc aattatagtt | 120 |
| cctcagggag aattcaatcg agtaaactct tcgcagaagt ccctggtttt tcaatttatc | 180 |
| accataccag attctgaact cgaggcaaat ggaccagtcg gtctctaaca cagctcaac | 240 |
| aaaattatgg aggcaagctt caaggactgt ataaggcagt tgttgaaaca acaaggcaat | 300 |
| gatattgcat gtatcatcta cgacgagttc atgtatttt gtggagccgt agctgaggag | 360 |
| ttgaagcttc ccaatttcat cttcagtact caaactgcta cacataaagt ttgctgcaat | 420 |
| gttttaagca aacttaatgc caagaagtac ttgatcgaca tggaagagca tgacgtgcaa | 480 |
| aacaaggtag tggaaaatat gcatccatta agatacaaag acttaccaac tgcaacattt | 540 |
| ggagaactag aacctttttt ggagctctgt agagatgtag tcaacaaaag aacagcctct | 600 |
| gctgttatca tcaacaccgt gacctgtcta gagagctcgt ctctcacaag gctgcaacaa | 660 |
| gaactccaaa ttccggtgta tccattaggc cctcttcaca ttacagattc atcgacagga | 720 |
| tttactgtgc tgcaagagga taggagctgc gttgaatggc tgaacaagca gaaaccaagg | 780 |
| tctgtcatat acataagttt aggaagcatg gttctcatgg aaaccaagga gatgttagag | 840 |
| atggcttggg gaatgttgaa tagcaaccaa cctttcttat gggtcatccg acctggatct | 900 |
| gtctcaggct ccgaggggat agagtcattg ccagaggaag tcagtaagat ggttttagag | 960 |
| aaaggataca ttgtgaaatg gcaccacaa atagaagtac taggacatcc ctcagtggaa | 1020 |
| ggcttttgga gccactgtgg atggaactca cactcgaga gcattgtgga aggagttcca | 1080 |
| atgatttgca ggcctatca aggcgagcag atgttaaatg caatatatct agagagtgta | 1140 |
| tggagaatag ggattcaggt aggaggtgaa ctggaaagag gagccgtcga gagagctgtg | 1200 |
| aagaggttga ttgtggataa agaaggtgca agcatgaggg agagaaccct tgttttaaaa | 1260 |
| gagaagctca aagcctctat tagaggtgga ggctcctcat gcaatgcatt agatgagctt | 1320 |
| gtcaagcact tgaagacaga gtgaatggag aaaagagtag agaagagaag gatagtgttg | 1380 |
| gttccacttc cattactagg acatttcact ccgatgatgc aactcggcca agcccttatc | 1440 |
| ttgaagggat tctcaattat agttcctcag ggagaattca atcgagtaaa ctcttcgcag | 1500 |

```
aagttccctg gttttcaatt tatcaccata ccagattctg aactcgaggc aaatggacca   1560
gtcgggtctc taacacagct caacaaaatt atggaggcaa gcttcaagga ctgtataagg   1620
cagttgttga acaacaagg caatgatatt gcatgtatca tctacgacga gttcatgtat    1680
ttttgtggag ccgtagctga ggagttgaag cttcccaatt tcatcttcag tactcaaact   1740
gctacacata aagtttgctg caatgtttta agcaaactta atgccaagaa gtacttgatc   1800
gacatggaag agcatgacgt gcaaaacaag gtagtggaaa atatgcatcc attaagatac   1860
aaagacttac caactgcaac atttggagaa ctagaacctt ttttggagct ctgtagagat   1920
gtagtcaaca aaagaacagc ctctgctgtt atcatcaaca ccgtgacctg tctagagagc   1980
tcgtctctca caaggctgca acaagaactc caaattccgg tgtatccatt aggccctctt   2040
cacattacag attcatcgac aggatttact gtgctgcaag aggataggag ctgcgttgaa   2100
tggctgaaca agcagaaacc aaggtctgtc atatacataa gtttaggaag catggttctc   2160
atggaaacca aggagatgtt agagatggct tggggaatgt tgaatagcaa ccaacctttc   2220
ttatgggtca tccgacctgg atctgtctca ggctccgagg ggatagagtc attgccagag   2280
gaagtcagta agatggtttt agagaaagga tacattgtga aatgggcacc acaaatagaa   2340
gtactaggac atccctcagt ggggaggcttt tggagccact gtggatggaa ctcaacactc   2400
gagagcattg tggaaggagt tccaatgatt tgcaggcctt atcaaggcga gcagatgtta   2460
aatgcaatat atctagagag tgtatggaga taggggattc aggtaggagg tgaactggaa   2520
agaggagccg tcgagagagc tgtgaagagg ttgattgtgg ataaagaagg tgcaagcatg   2580
agggagagaa cccttgtttt aaaagagaag ctcaaagcct ctattagagg tggaggctcc   2640
tcatgcaatg cattagatga gcttgtcaag cacttgaaga cagagtga              2688
```

<210> SEQ ID NO 26
<211> LENGTH: 447
<212> TYPE: PRT
<213> ORGANISM: Arabidopsis thaliana

<400> SEQUENCE: 26

```
Met Glu Lys Arg Val Glu Lys Arg Ile Val Leu Val Pro Leu Pro
1               5                   10                  15

Leu Leu Gly His Phe Thr Pro Met Met Gln Leu Gly Gln Ala Leu Ile
            20                  25                  30

Leu Lys Gly Phe Ser Ile Ile Val Pro Gln Gly Glu Phe Asn Arg Val
        35                  40                  45

Asn Ser Ser Gln Lys Phe Pro Gly Phe Gln Phe Ile Thr Ile Pro Asp
    50                  55                  60

Ser Glu Leu Glu Ala Asn Gly Pro Val Gly Ser Leu Thr Gln Leu Asn
65                  70                  75                  80

Lys Ile Met Glu Ala Ser Phe Lys Asp Cys Ile Arg Gln Leu Leu Lys
                85                  90                  95

Gln Gln Gly Asn Asp Ile Ala Cys Ile Ile Tyr Asp Glu Phe Met Tyr
            100                 105                 110

Phe Cys Gly Ala Val Ala Glu Glu Leu Lys Leu Pro Asn Phe Ile Phe
        115                 120                 125

Ser Thr Gln Thr Ala Thr His Lys Val Cys Cys Asn Val Leu Ser Lys
    130                 135                 140

Leu Asn Ala Lys Lys Tyr Leu Ile Asp Met Glu Glu His Asp Val Gln
145                 150                 155                 160

Asn Lys Val Val Glu Asn Met His Pro Leu Arg Tyr Lys Asp Leu Pro
```

```
                165                 170                 175
Thr Ala Thr Phe Gly Glu Leu Glu Pro Phe Leu Glu Leu Cys Arg Asp
            180                 185                 190

Val Val Asn Lys Arg Thr Ala Ser Ala Val Ile Ile Asn Thr Val Thr
        195                 200                 205

Cys Leu Glu Ser Ser Ser Leu Thr Arg Leu Gln Gln Glu Leu Gln Ile
    210                 215                 220

Pro Val Tyr Pro Leu Gly Pro Leu His Ile Thr Asp Ser Ser Thr Gly
225                 230                 235                 240

Phe Thr Val Leu Gln Glu Asp Arg Ser Cys Val Glu Trp Leu Asn Lys
                245                 250                 255

Gln Lys Pro Arg Ser Val Ile Tyr Ile Ser Leu Gly Ser Met Val Leu
            260                 265                 270

Met Glu Thr Lys Glu Met Leu Glu Met Ala Trp Gly Met Leu Asn Ser
            275                 280                 285

Asn Gln Pro Phe Leu Trp Val Ile Arg Pro Gly Ser Val Ser Gly Ser
            290                 295                 300

Glu Gly Ile Glu Ser Leu Pro Glu Glu Val Ser Lys Met Val Leu Glu
305                 310                 315                 320

Lys Gly Tyr Ile Val Lys Trp Ala Pro Gln Ile Glu Val Leu Gly His
                325                 330                 335

Pro Ser Val Gly Gly Phe Trp Ser His Cys Gly Trp Asn Ser Thr Leu
            340                 345                 350

Glu Ser Ile Val Glu Gly Val Pro Met Ile Cys Arg Pro Tyr Gln Gly
            355                 360                 365

Glu Gln Met Leu Asn Ala Ile Tyr Leu Glu Ser Val Trp Arg Ile Gly
            370                 375                 380

Ile Gln Val Gly Gly Glu Leu Glu Arg Gly Ala Val Glu Arg Ala Val
385                 390                 395                 400

Lys Arg Leu Ile Val Asp Lys Glu Gly Ala Ser Met Arg Glu Arg Thr
                405                 410                 415

Leu Val Leu Lys Glu Lys Leu Lys Ala Ser Ile Arg Gly Gly Gly Ser
                420                 425                 430

Ser Cys Asn Ala Leu Asp Glu Leu Val Lys His Leu Lys Thr Glu
            435                 440                 445
```

GLYCOSYLATED AMINOCOUMARINS AND METHODS OF PREPARING AND USES OF SAME

CROSS-REFERENCE TO RELATED APPLICATIONS

This application is the U.S. national stage application of International Patent Application No. PCT/GB2011/052006, filed Oct. 17, 2011, which claims priority to United Kingdom Application No. 1017450.6, filed Oct. 15, 2010, the disclosures of each of which are incorporated herein by reference in their entirety.

FIELD OF THE INVENTION

The present invention relates to methods of glycosylating aminocoumarins, novel glycosylated aminocoumarins obtained by said methods, and novel uses of said aminocoumarins in therapy.

BACKGROUND OF THE INVENTION

Aminocoumarin antibiotics such as Novobiocin, Coumermycin A1 and Clorobiocin act as bacterial DNA gyrase inhibitors and also possess anticancer activity by binding to the HSP90 chaperone. The 3-amino-4,7-dihydrocoumarin ring is the core moiety present in all of these antibiotics. They bind with high affinity to the GyrB subunit of the DNA gyrase enzyme. The usefulness of aminocoumarins is limited by poor water solubility and poor oral absorption, mainly due to the hydrophobic nature of these antibiotics.

Glycosyltransferase (GT) catalyses the transfer of sugar moieties from active donor molecules to specific acceptor molecules forming glycosidic bond. GTs are important tools in the synthesis of drugs. An increasing appreciation of carbohydrates as components of natural products has uncovered new opportunities in carbohydrate-based drug design. The exact identity and pattern of glycosyl moieties can influence pharmacology/pharmacokinetics, invoke biological specificity at the molecular/tissue/organism level and even define the precise mechanism of action.

SUMMARY OF THE INVENTION

In a first aspect of the invention, there is provided a method of glycosylating an aminocoumarin compound comprising conjugating a sugar to the 4'-OH position of the core of the aminocoumarin compound.

In a second aspect of the invention, there is provided an aminocoumarin compound glycosylated at the 4'-OH position of the core of the aminocoumarin compound. Further aspects of this invention provide this compound for use in therapy, more particularly for use as an antibiotic, or in anti-cancer treatment.

We have shown that glycosylation can improve anticancer activity, and can alter the antibacterial activity (e.g. convert an agent from bacteriostatic to bactericidal).

Furthermore, glycosylation advantageously improves aspects of the amino-coumarins compounds such as their toxicity, resistance, solubility and stability.

WO 2006/003456 discloses methods of attaching a sugar to a substrate comprising contacting the substrate with a macrolide glycoyltransferase enzyme in the presence of a sugar donor. The substrate may be a macrolide antibiotic or coumarin. Antibiotics are specifically mentioned in claim 12. However, macrolide enzymes will not conjugate a sugar at the 4'-OH position of an aminocoumarin. This is evidenced by Yang et al in J. Am, Chem. Soc. 2005, 127, 9336-9337, and the supporting information. Compounds 45 and 46 are novobiocin and coumermycin A1 respectively. Pages 57-58, FIGS. 11a, 11b and 11c demonstrate the activities of MGTs against different acceptors. All of the plates with compounds 45 and 46 were red in colour, indicating that none of the MGTs could act on these compounds.

DESCRIPTION OF THE SEQUENCE LISTING

Figure 1:
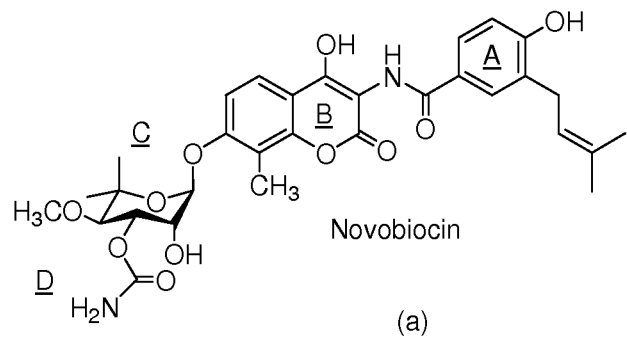
FIG. 1 shows the structures of novobiocin, clorobiocin and coumermycin A1.
Figure 1:
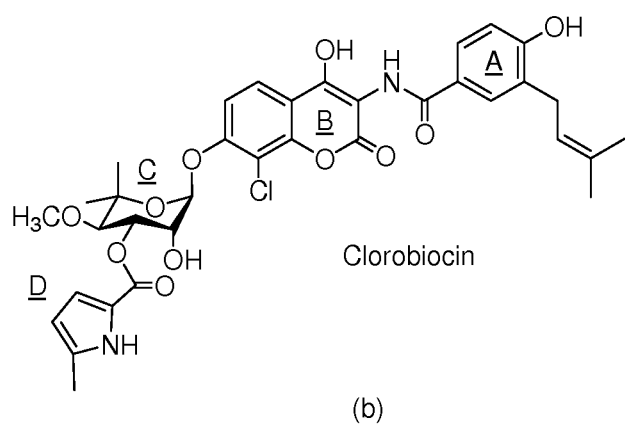
Figure 1:
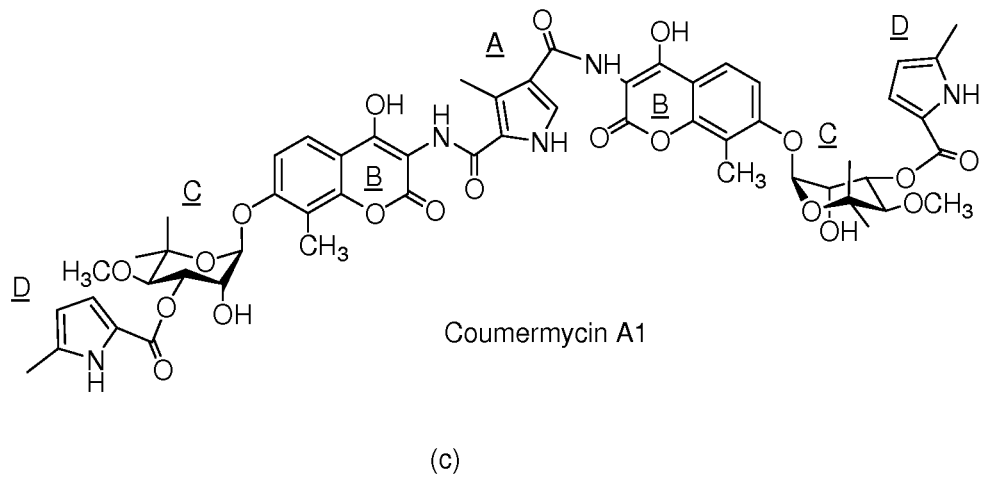

SEQ ID NO 1 is UGT78D2 (DNA)
SEQ ID NO 2 is UGT78D2 (amino acid)
SEQ ID NO 3 is UGT71B1 (DNA)
SEQ ID NO 4 is UGT71B1 (amino acid)
SEQ ID NO 5 is UGT71B8 (DNA)
SEQ ID NO 6 is UGT71B8 (amino acid)
SEQ ID NO 7 is UGT88A1 (DNA)
SEQ ID NO 8 is UGT88A1 (amino acid)
SEQ ID NO 9 is UGT73C6 (DNA)
SEQ ID NO 10 is UGT73C6 (amino acid)
SEQ ID NO 11 is UGT73C5 (DNA)
SEQ ID NO 12 is UGT73C5 (amino acid)
SEQ ID NO 13 is UGT73C1 (DNA)
SEQ ID NO 14 is UGT73C1 (amino acid)
SEQ ID NO 15 is UGT76E1 (DNA)
SEQ ID NO 16 is UGT76E1 (amino acid)
SEQ ID NO 17 is UGT73B3 (DNA)
SEQ ID NO 18 is UGT73B3 (amino acid)
SEQ ID NO 19 is UGT73B4 (DNA)
SEQ ID NO 20 is UGT73B4 (amino acid)
SEQ ID NO 21 is 20n10 (DNA)
SEQ ID NO 22 is 20n10 (amino acid)
SEQ ID NO 23 is UGT76E4 (DNA)
SEQ ID NO 24 is UGT76E4 (amino acid)
SEQ ID NO 25 is UGT76E3 (DNA)
SEQ ID NO 26 is UGT76E3 (amino acid)

DETAILED DESCRIPTION OF INVENTION

In the method according to the first aspect of this invention, a chemical or an enzymatic conjugation reaction may occur. The reaction is glycosylation, i.e. addition of a sugar moiety to the aminocoumarin. Enzymes particularly useful in the invention include plant glycosyltransferases and, in particular the UDP-glycosyltransferases (UGTs), for instance from *Arabidopsis thaliana* or Oat. UGTs in this family from groups E, D, F and H are particularly preferred. Sugar donors such as UDP-glucose may be used. The use of α-UDPglucose is particularly preferred. Suitable GTs include UGT78D2, 71B8, 71B1, 88A1, 73C5, 73C6, 73C1, 73B3, 73B4, 76E1, 76E4 and 76E3 from *Arabidopsis Thaliana* and 20n10 from Oat. Glycosyltransferases from *Arabidopsis* are described in Genome Biol. Vol 2 No 2, pp 3004.1-3004.6, 2001 and Glycobiology Vol 13 No 3, pp 139-145, 2003. Those from oat are described in PNAS, May 25, 2004, Vol. 101, No. 21 8233-8238.

The enzymatic method of the invention is carried out using a plant glycosyltransferase. These enzymes catalyze the addition of glycosyl group from a UDP-sugar to an aminocoumarin at the 4'-OH position. Suitable enzymes include, but are not limited those expressed in *E. Coli*.

Plant enzymes in accordance with the invention include the polypeptides shown in SEQ ID NOs 2, 4, 6, 8, 10, 12, 14, 16, 18, 20, 22, 24 or 26 and variants thereof.

A variant is an enzyme having an amino acid sequence which varies from that of UGT78D2 (SEQ ID NOs 2), 71B8 (SEQ ID NOs 4), 71B1 (SEQ ID NOs 6), 88A1 (SEQ ID NOs 8), 73C6 (SEQ ID NOs 10), 73C5 (SEQ ID NOs 12), 73C1 (SEQ ID NOs 14), 73B3 (SEQ ID NOs 16), 73B4 (SEQ ID NOs 18), 76E1 (SEQ ID NOs 20), 76E4 (SEQ ID NO 24) or 76E3 (SEQ ID NO 26) from *Arabidopsis Thaliana* and 20n10 (SEQ ID NOs 22) from Oat.

A variant of any of SEQ ID NOs 2, 4, 6, 8, 10, 12, 14, 16, 18, 20, 22, 24 or 26 may be a naturally occurring variant which is expressed by organism. Such variants may be identified by looking for aminocoumarin activity in those strains which have a sequence which is highly conserved compared to any of the SEQ ID NOs 2, 4, 6, 8, 10, 12, 14, 16, 18, 20, 22, 24 or 26. Such proteins may be identified by analysis of the polynucleotide encoding such a protein isolated from another organism, for example, by carrying out the polymerase chain reaction using primers derived from portions of any of SEQ ID NOs: 1, 3, 5, 7, 9, 11, 13, 15, 17, 19, 21, 23 or 25.

Variants of any of SEQ ID NOs 2, 4, 6, 8, 10, 12, 14, 16, 18, 20, 22, 24 or 26 include sequences which vary from SEQ ID NOs 2, 4, 6, 8, 10, 12, 14, 16, 18, 20, 22, 24 or 26 but are not necessarily naturally occurring plant GTs. Over the entire length of the amino acid sequence of any of SEQ ID NOs 2, 4, 6, 8, 10, 12, 14, 16, 18, 20, 22, 24 or 26. A variant will preferably be at least 35% homologous to that sequence based on amino acid identity. More preferably, the polypeptide may be at least 40%, at least 50%, at least 60%, at least 70%, at least 80% or at least 90% and more preferably at least 95%, 97% or 99% homologous based on amino acid identity to the amino acid sequence of any of SEQ ID NOs 2, 4, 6, 8, 10, 12, 14, 16, 18, 20, 22, 24 or 26, over the entire sequence. There may be at least 80%, for example at least 85%, 90%, 95% amino acid identity over a stretch of 40 or more, for example 60, 100 or 120 or more, contiguous amino acids ("hard homology").

Amino acid substitutions may be made to the amino acid sequence of any of SEQ ID NOs 2, 4, 6, 8, 10, 12, 14, 16, 18, 20, 22, 24 or 26, for example up to 1, 2, 3, 4, 5, 10, 20, or 30 substitutions. Conservative substitutions may be made, for example, according to the following table. Amino acids in the same block in the second column and preferably in the same line in the third column may be substituted for each other:

| NON-AROMATIC | Non-polar | G A P |
| --- | --- | --- |
| | | I L V |
| | Polar-uncharged | C S T M |
| | | N Q |
| | Polar-charged | D E |
| | | H K R |
| AROMATIC | | H F W Y |

One or more amino acid residues of the amono acid sequence of any of SEQ ID NOs 2, 4, 6, 8, 10, 12, 14, 16, 18, 20, 22, 24 or 26 may alternatively or additionally be deleted. Up to 1, 2, 3, 4, 5, 10, 20, 30 residues may be deleted, or more. Variants of any of SEQ ID NOs 2, 4, 6, 8, 10, 12, 14, 16, 18, 20, 22, 24 or 26 include fragments of those sequences. Such fragments retain aminocoumarin activity. Fragments may be at least 100, 200, 250, 300, 350 or 400 amino acids in length. Such fragments may be used to produce chimeric enzymes as described in more detail below. A fragment preferably comprises the catalytic domain of any of SEQ ID NOs 2, 4, 6, 8, 10, 12, 14, 16, 18, 20, 22, 24 or 26.

Variants of any of SEQ ID NOs 2, 4, 6, 8, 10, 12, 14, 16, 18, 20, 22, 24 or 26 include chimeric proteins comprising fragments or proteins of any SEQ ID NOs 2, 4, 6, 8, 10, 12, 14, 16, 18, 20, 22, 24 or 26.

One or more amino acids may be alternatively or additionally added to the polypeptides described above. An extension may be provided at the N-terminus or C-terminus of the amino acid sequence of any of SEQ ID NOs 2, 4, 6, 8, 10, 12, 14, 16, 18, 20, 22, 24 or 26 or polypeptide variant or fragment thereof. The extension may be quite short, for example, from 1 to 10 amino acids in length. Alternatively, the extension may be longer, for example up to 50 or 100 amino acids. A carrier protein may be fused to an amino acid sequence according to the invention.

Preferred variants (mutants) of plant glycosyl transferases according to the invention are:

73C5D397E (+)

73C6D397E (+)

73C1D393E (−)

73B4Q374H (−)

73B3Q397H (−)

37C1Q394H (−)

88A1Q384H (+)

71B8Q390H (−)

76E4Q375H (−)

73C1D393EQ394H (+)

The nomenclature used to label the mutants is as follows: 73C5D397E means that the wild type enzyme is UGT73C5 (the sequence for which is known, and provided herein), wherein the amino acid D (aspartic acid) has been replaced by E (glutamic acid) at position 397.

Those mutants followed by a "(+)" are particularly preferred as, not only can they use UDP-glucose as a donor, but they can additional use UDP-galactose as a donor.

The mutants are preferably synthesised using site-directed mutagenesis. Such procedures are known to the person skilled in the art.

Generally, the aminocoumarin compounds used in this invention have the following formula:

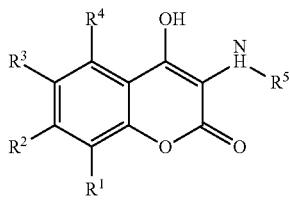

$R^1$, $R^3$ and $R^4$ are each independently selected from H, OH, $C_{1-20}$ alkyl, $C_{1-20}$ alkenyl, amino, or a halogen;
$R^2$ is an optionally substituted sugar moiety;
$R^5$ is selected from aryl, heteroaryl, $C_{1-20}$ alkyl, $C_{1-20}$ alkenyl, H, or $C(=O)R^6$,
wherein $R^6$ is selected from the same groups as $R^5$ or is halo, amino, or OH.

The aminocoumarin compounds preferably have the following core:

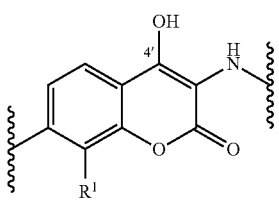

In this formula, $R^1$ is an optionally substituted $C_{1-20}$ alkyl group, hydroxyl, amino or halo group. Preferably, $R^1$ is methyl, or Cl. If $R^1$ is a hydroxyl group, it may be protected with a hydroxyl protecting group.

Preferred amino coumarins have general formula:

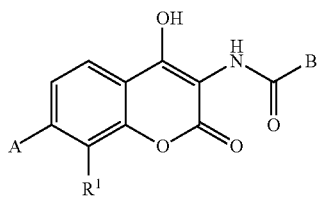

In this formula, A is generally a sugar moiety, which may be optionally substituted, and B is generally optionally substituted aryl, heteroaryl, a $C_{1-20}$ alkyl or $C_{1-20}$ alkenyl. Any aryl or heteroaryl rings may be monocyclic or multi-cyclic. $R^1$ is an optionally substituted $C_{1-20}$ alkyl group, hydroxyl, amino or halo group. Preferably, $R^1$ is methyl or Cl.

Suitable optional substituents for the compounds in this invention include any of the groups listed above for the A, $R^1$ and B groups, carboxy and ester groups. Other possible substituents include $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

Novobiocin, Clorobiocin and Coumermycin A1 are the three most important aminocoumarin antibiotics produced from various *Streptomyces* strains. These aminocoumarins share a 3-amino-4,7-dihydroxycoumarin moiety and are shown in FIG. 1. Novobiocin (FIG. 1-*a*) has a 4-hydroxybenzoate moiety and a deoxy sugar, i.e. a noviose moiety which is essential for biological activity whereas Coumermycin A1 (FIG. 1-*c*) contains two coumarin noviose moieties attached together by 3-methyl-2,4-dicarboxylpyrrole and also a 5-methyl-2-pyrrolecarbonyl substitution on the noviose moieties. The Novobiocin chemical structure can be divided into three distinct entities: 3-dimethylallyl-4-hydroxybenzoyl moiety (ring A), a 3-amino-4,7-dihydroxy-coumarin moiety (ring B) substituted with a methyl group and finally a substituted deoxysugar (ring C) with its 3"-OH esterified with carbamoyl group The sub-entity consisting of noviose plus coumarin moiety is referred to as novenamine; the sub entity consisting of a coumarin plus the benzoic acid derivative is referred to as novobiocic acid.

Typically, in this invention, coumermycin A1 is enzymatically glycosylated, and novobiocin can be both chemically and enzymatically glycosylated.

Figure 2:
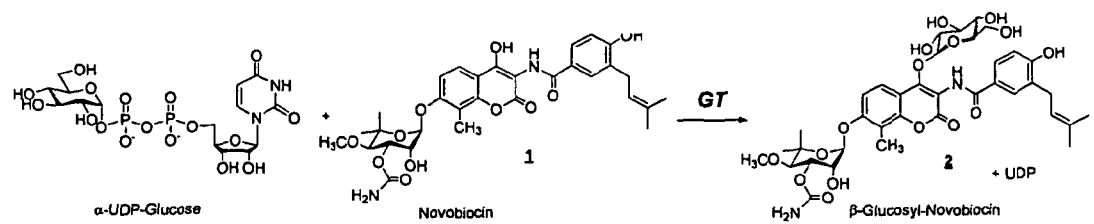
FIG. 2 shows the enzymatic reaction with novobiocin.
Figure 2:
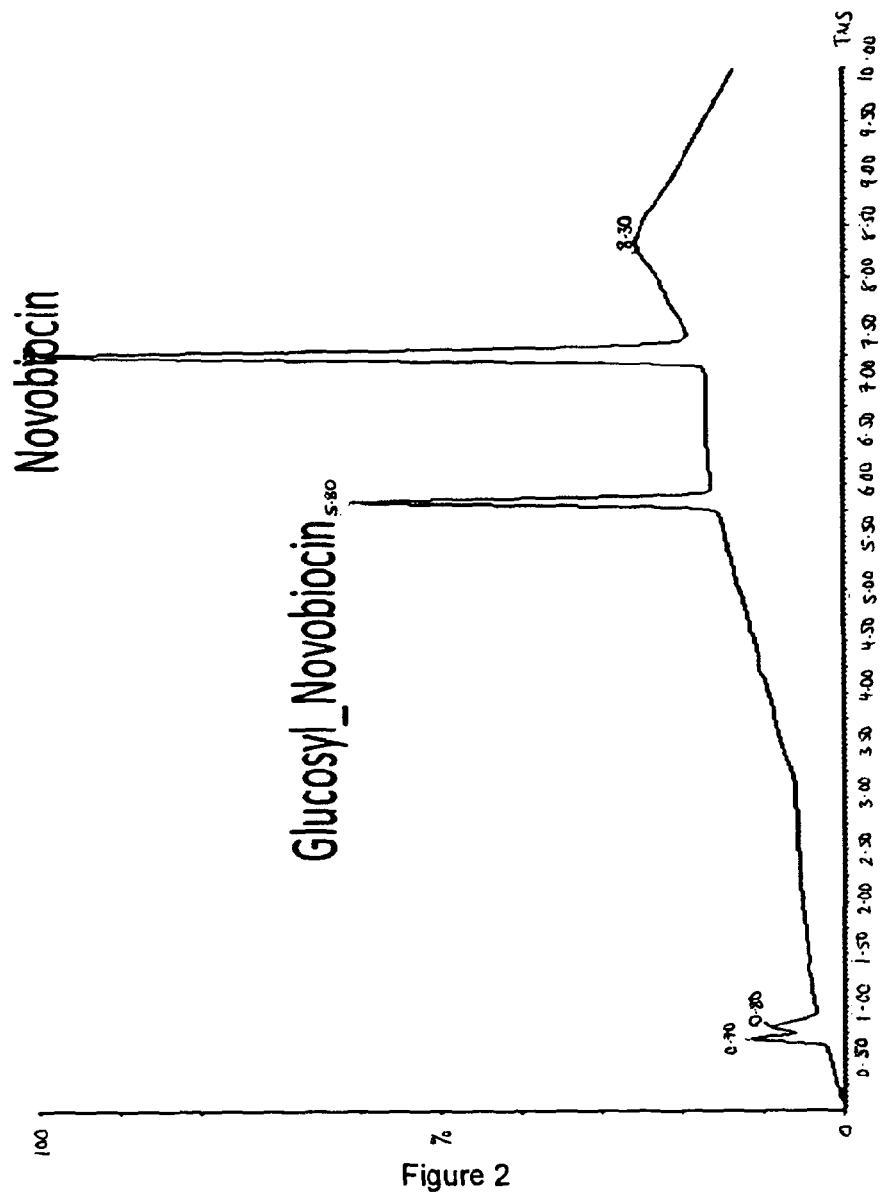

The enzymatic reaction with novobiocin is shown in FIG. 2, together with the LC/MS specimen of biocatalysis of novobiocin using GT.

Suitable sugars for use in this invention include but are not limited to monosaccharides, disaccharides, and polysaccharides, substances derived from the monosaccharides by oxidation of one or more terminal groups to carboxylic acid and substrates derived from monosaccharides by replacement of one or more hydroxyl groups by a hydrogen atom, an amino group, a thiol group or similar heteroatomic groups.

In one embodiment, the sugar is a monosaccharide. Monosaccharides are polyhydroxy aldehydes (H—(CHOH)$_n$) —CHO) or polyhydroxyl ketones (H—(CHOH)$_n$—CO—(CHOH)$_m$—H) with three (triose), four (terose), five (pentose), six (hexose), seven (heptose) or more carbon atoms. The monosaccharide may have a terminal, i.e. aldehydic, (potential) carbonyl group (aldose) or a nonterminal, i.e. ketonic, (potential) carbonyl group (ketose). The monosaccharides have more than one (potential) carbonyl group, i.e. may be a daildose, diketose or aldoketose. A potential carbonyl group is a hemiacetal group that arises from the formation of a ring structure.

The monosaccharide may form a ring structure and be a cyclic hemiacetal or hemiketal. Cyclic forms include oxiroses ($C_3$), Oxetoses ($C_4$), furanoses ($C_5$) pyranoses ($C_6$), septanoses ($C_7$) and octanoses ($C_8$). The position at which the ring closes may vary.

Monosaccharides may also be modified at various positions, such modifications include, but are not limited to, substitution of an alcoholic hydroxyl group with hydrogen (deoxy sugar), substitution of an alcoholic hydroxyl group or a ring oxygen with an amino group (amino sugar), substitution of a hydroxyl by thiol or a ring oxygen with sulphur (thiosugar), substitution with selenium (selenosugar), substitution of a ring carbon with nitrogen (azasugar), substation of a aldehydic group with a carboxyl group (aldonic acid), substitution of a carbonyl group with an alcoholic group (aldonic acid or ketoaldonic acid) and oxidizing an aldoxe or aldose derivative to a carboxyl group (uronic acid).

Suitable monosaccharides include, but are not limited to, arabinose, ribose, ribulose, xylose, xyulose, lyxose, allose, altrose, glucose (Glc), N-acetylglucosamine (GlcNAc), N-acetylgalacotosamine (GalNAc), fructose (Frc), galactose (Gal), fucose (Fuc), gulose, idose, mannose (Man), sorbose, talose, tagatose, sialic acid, glucuronoic acid and iduronic acid. Preferred monosaccharides are glucose, galactose and mannose. More preferred monosaccharides are glucose and galactose. Preferred sugar donors for enzymatic reactions include, but a not limited to, UDPGlc, UDPGal, UDPGlcNAc, GDPMan, UDPXyl, UDP5S-Glc, UDPMan. These monosaccharides and sugar donors may be modified as set forth above.

In another embodiment, the sugars comprise a disaccharide. Disaccharides may be derived from the combination of any two of the monosaccharides described above. Suitable disaccharides include, but a not limited to, sucrose (Suc), lactose (Lac), maltose (Mal), isomaltose (Isomal), trehalose (Tre) and cellobiose.

In another embodiment, the sugar donor comprises a polysaccharide. Polysaccharides are derived from the combination of three or more (for example, 20, 30, 50, 100, 200 or more) monosaccharide units. Suitable polysaccharides include, but are not limited to starch, amylase, amylopectin, glycogen, insulin, cellulose, chitin, glycosaminoglycans, agar, carrageenan, pectin, xantham gum and glucomannan.

Further examples of suitable sugars are given in WO 2006/003456.

When the sugar is chemically conjugated to the aminocoumarin Helferich conditions may be used (ie. using $Hg(CN)_2$ as a catalyst). A glycosyl halide may be used as a glycosyl donor. Glycosyl bromides are preferred.

Figure 3:
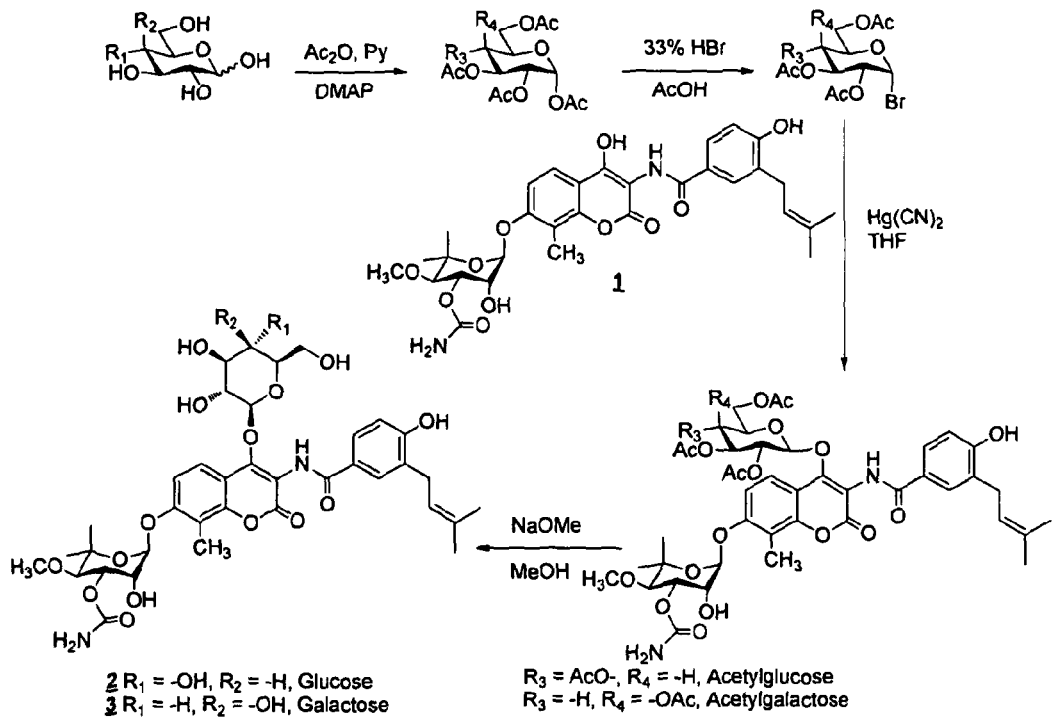
FIG. 3 shows glycosyl_novobiocins, with both glucosyl and galactosyl modifications, synthesised in four steps.

Chemical glycosylation of novobiocin is illustrated in FIG. 3, which shows glycosyl-novobiocins, with both glucosyl and galactosyl modifications, synthesised in four steps.

A Lewis acid may be used to promote glycosylation. 2,3,4,6-tetra-O-acetyl-α-D-glucopyranosyl bromide may be used, with 2,3,4,6-tetra-O-acetyl-α-D-galactopyranosyl bromide as glycosyl donor. $Hg(CN)_2$ used as a catalyst, has been found to promote the 1,2-trans-glycosylation of aminocoumarin novobiocin with THF as solvent both at room temperature and below zero degrees in a stereo-controlled manner with reasonable high yields.

Reactive functional groups on the glycosyl donor/acceptor can be protected to provide regio-selectivity. Protecting groups on both the glycosyl donor/acceptor can affect reactivity and yield of the glycosylation reaction. Electron withdrawing groups such as acetyl and benzoyl reduce the reactivity of the donor or acceptor, and are therefore referred to as "disarming groups" whereas electron donating groups such as benzyl increase the reactivity of the donor or acceptor, and therefore referred to as "arming groups".

With regard to Novobiocin in a particular, it is known that this is a dibasic acid with $pK_a$ values of 4.3 and 9.1. These values ensure that the —OH group on the coumarin ring (Ring B) is more reactive than the —OH on benzoic acid derivative (Ring A). For this reason the hydroxyl ring B is thermodynamically more likely to undergo glycosylation than the hydroxyl on ring A.

However, even with Novobiocin, it is still necessary to activate the glycosyl donor. Before a sugar molecule can be coupled to aglycone during glycosylation it must be activated into a glycosyl donor. This can be done by protecting —OH groups on the sugar molecule with acetyl groups and then brominating the anomeric carbon. Alternative protecting group chemistries can be used, for instance, methyl groups, and benzoyl groups. However, acetyl groups are preferred as acetyl can easily be introduced and removed from molecules. Acetyl groups are participating groups, so can help enhance the stereo-selectivity during the formation of a glycosidic bond. Furthermore, acetyl groups have good solubility in organic solvents and can easily be crystallized.

The aminocoumarins compounds of the invention may be used in therapy, to treat the same conditions as the un-conjugated compounds. For instance, the aminocoumarins compounds may be used as antibiotics to treat bacterial infections, or in anticancer treatment. Suitable formulations of these compounds are known to those skilled in the art.

The invention will now be illustrated by the following Examples.

EXAMPLES

Example 1

Biocatalysis

Glucosyl_novobiocin was isolated from UGT73C5 catalyzed reaction using an HPLC with the following procedure:
Solvent A: 99.9% $H_2O$+0.1% formic acid
Solvent B: 99.9% MeOH+0.1% Formic acid
0-1 minutes: 1% B; 1-3 minutes: 50% B, 3-4 minutes: 50% B, 4-14 minutes: 95% B, 14-19 minutes: 95% B, 19-20 minutes: 1% B. Flow rate, 1.5 mL/min, Column: Agilent, ElipseXDB-C18, 5 μM. Retention time: 14.5 min.

A LC/MS spectrum of biocatalysis of novobiocin using GT was produced (see FIG. 2). In addition $MS^n$ spectra were produced and these indicated the glycosylation position. A peak was present at 773 which indicated the formation of glucosylated Novobiocin by glycosyltransferase. The glycosylation position can be determined by $MS^n$. The $MS^4$ (773→730→556→368, 394) indicates the formation of peak at 368 which provides proof of the structure. The structure was further confirmed by NMR.

Example 2

Chemical Glycosylation of Novobiocin

Glycosyl_novobiocins, with both glucosyl and galactosyl modifications, have been synthesized in four steps. Higher yield and pure stereochemistry products have been obtained via Helferish coupling (see FIG. 3). These steps are detailed below:

Synthesis of β-4'-O-(2,3,4,6-tetra-acetyl glucosyl) Novobiocin

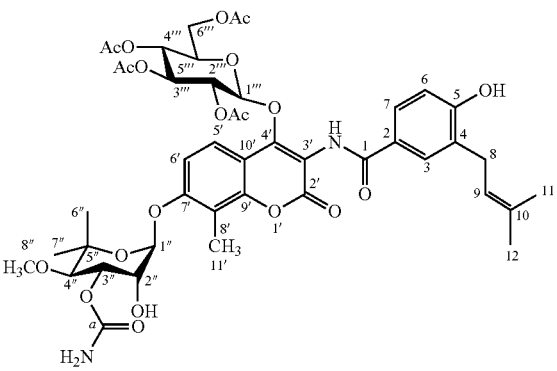

α-1-Bromine-2,3,4,6-tetra-O-acetyl-D-glucose (285 mg, 0.69 mmol) was added to Novobiocin (1, 400 mg, 0.63 mmol), $Hg(CN)_2$ (159 mg, 0.17 mmol) 4 Å molecular sieve and THF (20 mL) and stirred for 7 days at 0° C. and covered with foil. Solid was removed and disposed carefully. Organic was wash with KI (2M, 2*20 mL), saturated NaHCO$_3$ (2*10 mL) and dried with MgSO$_4$. Organic solvent was removed under reduced pressure after filtration. Residue was purified by flash column (Ethyl acetate: Petroleum Ether: MeOH 16:4:1 v/v/v, Rf=0.3) gave a white powered (520 mg, yield 87%). $^1$H-NMR (500 MHz, CD$_3$OD): δ=7.81 (1H, d, J=2.0 Hz, H3), 7.77 (1H, dd, J=2.4, 8.4 Hz, H5'), 7.71 (1H, d, J=9.6 Hz, H7), 7.27 (1H, d, J=9.2 Hz, H6'), 6.90 (1H, d, J=8.4 Hz, H6), 5.63 (1H, d, J=3.2 Hz, H1"), 5.60 (1H, d, J=7.6 Hz, H1'''), 5.39 (1H, m, H3"), 5.36 (1H, m, H9), 5.30 (1H, t, J=8.0 Hz, H3'''), 5.26 (1H, t, J=9.2 Hz, H2'''), 5.12 (1H, t, J=9.2 Hz, H4'''), 4.27 (1H, t, J=2.5 Hz, H2"), 4.08 (1H, dd, J=4.1, 13.2 Hz, H6'''), 3.78 (1H, dd, J=2.4, 12.4 Hz, H6'''), 3.63 (1H, m, H5'''), 3.61 (1H, m, H4"), 3.58 (3H, s, H8"), 3.33 (2H, m, H8), 2.34 (3H, s, H11'), 1.99 (3H, s, C$\underline{H}_3$CO), 1.98 (3H, s, C$\underline{H}_3$CO), 1.92 (3H, s, CH$_3$CO), 1.89 (3H, s, C$\underline{H}_3$CO), 1.78 (6H, s, H11, H12), 1.32 (3H, s, H6"), 1.17 (3H, s, H7"); $^{13}$CNMR (125 MHz, CD$_3$OD): δ=171.5 (4*CH$_3$$\underline{C}$O), 170.0 (C1), 162.9 (Ca), 161.0 (C2'), 160.8 (C4'), 159.5 (C9'), 159.1 (C2), 152.2 (C7'), 133.8 (C10), 130.9 (C3), 130.0 (C5), 128.6 (C5'), 125.1 (C4), 123.6 (C7), 123.3 (C9), 115.7 (C6), 115.3 (C8'), 112.2 (C10'), 111.9 (C6'), 108.9 (C3') 101.2 (C1'''), 100.2 (C1"), 82.6 (C4"), 80.2 (C5"), 73.9 (C5'''), 73.6 (C2'''), 73.0 (C3'''), 72.8 (C3"), 70.9 (C2"), 69.1 (C4'''), 62.0 (C8"), 61.3 (C6'''), 29.3 (C8), 29.1 (C6"), 26.1 (C11), 23.3 (C7"), 20.6 (4*$\underline{C}$H$_3$CO), 18.1 (C12), 8.7 (C11'). HMBC in dicated that H1''' coupled to C4'. HRMS m/z 943.3335 ([M+H$^+$]$^+$) (Calc. 943.3348).

Synthesis of β-4'-O-glucosyl Novobiocin (2)

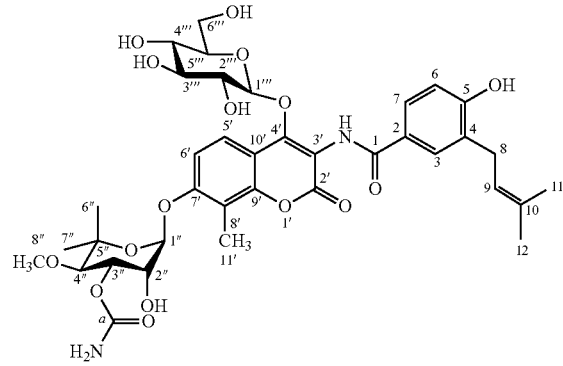

β-4'-O-(2,3,4,6-tetra-acetyl glucosyl)

Novobiocin (94 mg, 0.1 mmol) were dissolved in anhydrous MeOH (10 mL). NaOMe (1 mg, 0.02 mmol) was added and stirred for 1 minute at room temperature. Solvent was removed under reduced pressure and purified by HPLC as above gave white power (50 mg, 0.06 mmol, with 65% yield). $^1$H-NMR (500 MHz, CD$_3$OD): δ=7.79 (1H, d, J=9.1 Hz, H5'), 7.76 (1H, s, H3), 7.74 (1H, d, J=7.8 Hz, H7), 7.58 (1H, d, J=9.0 Hz, H6'), 7.16 (1H, d, J=9.6 Hz, H6), 5.51 (1H, d, J=2.7 Hz, H1"), 5.31 (1H, t, J=6.6 Hz, H9), 5.26 (1H, dd, J=3.3, 9.9 Hz, H3"), 4.99 (1H, d, J=8.7 Hz, H1'''), 4.17 (1H, t, J=2.7 Hz, H2"), 3.85 (1H, dd, J=2.1, 11.7 Hz, H6'''), 3.65 (1H, dd, J=5.3, 12.0 Hz, H6'''), 3.52 (1H, m, H5'''), 3.52 (1H, m, H4"), 3.50 (1H, m, H4'''), 3.49 (3H, s, H8"), 3.48 (1H, m, H3'''), 3.42 (1H, m, H2'''), 3.24 (2H, m, H8), 2.25 (3H, s, H11'), 1.68 (6H, s, H11, H12), 1.28 (3H, s, H6"), 1.09 (3H, s, H7"); $^{13}$CNMR (125 MHz, CD$_3$OD): δ=169.0 (C1), 160.1 (Ca), 159.8 (C2'), 159.3 (C4'), 158.8 (C2), 157.7 (C9'), 151.6 (C7'), 132.6 (C10), 132.1 (C5), 129.5 (C4), 129.1 (C3), 128.9 (C6'), 126.8 (C5'), 122.9 (C9), 122.2 (C7), 115.1 (C6), 114.1 (C8'), 113.1 (C10'), 109.3 (C3') 100.7 (C1'''), 99.2 (C1"), 81.2 (C4"), 78.1 (C5"), 76.9 (C3'''), 76.4 (C4'''), 72.5 (C3"), 69.9 (C2"), 69.8 (C2'''), 60.9 (C8"), 60.9 (C6'''), 60.8 (C5'''), 28.1 (C8), 28.0 (C7"), 24.8 (C11), 21.8 (C6"), 16.8 (C12), 7.6 (C11'). HMBC in dicated that H1''' coupled to C4'. HRMS m/z 797.2787 ([M+Na$^+$]$^+$) (Calc. 797.2745).

Synthesis of β-4'-O-(2,3,4,6-tetra-acetyl galactosyl) Novobiocin

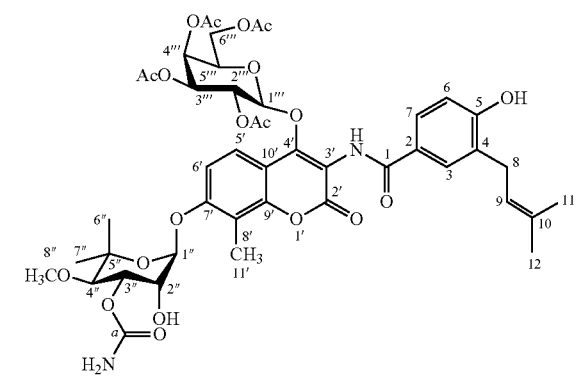

α-1-Bromine-2,3,4,6-tetra-O-acetyl-D-galactose (285 mg, 0.69 mmol) was added to Novobiocin (1, 400 mg, 0.63 mmol), Hg(CN)$_2$ (159 mg, 0.17 mmol) 4 Å molecular sieve and THF (20 mL) and stirred for 7 days at 0° C. and covered with foil. Solid was removed and disposed carefully. Organic was wash with KI (2M, 2*20 mL), saturated NaHCO$_3$ (2*10 mL) and dried with MgSO$_4$. Organic solvent was removed under reduced pressure after filtration. Residue was purified by flash column (Ethyl acetate: Petroleum Ether: MeOH 16:4:1 v/v/v, Rf=0.3) gave a white powered (250 mg, yield 42%). $^1$H-NMR (500 MHz, CD$_3$OD): δ=7.68 (1H, d, J=1.8 Hz, H3), 7.65 (1H, dd, J=1.4, 7.8 Hz, H5'), 7.55 (1H, d, J=9.6 Hz, H7), 7.13 (1H, d, J=8.7 Hz, H6'), 6.76 (1H, d, J=8.6 Hz, H6), 5.50 (1H, d, J=2.5 Hz, H1"), 5.45 (1H, d, J=8.1 Hz, H1'''), 5.33 (1H, dd, J=7.9, 10.3 Hz, H2'''), 5.24 (1H, m, H3"), 5.21 (1H, m, H4"), 5.22 (1H, m, H9), 5.01 (1H, dd, J=3.3, 10.3 Hz, H3'''), 4.14 (1H, t, J=2.5 Hz, H2"), 3.89 (1H, dd, J=7.6, 10.3 Hz, H6'''), 3.72 (1H, m, H5'''), 3.56 (1H, J=5.1, 10.5 Hz, H6'''), 3.47 (1H, m, H4"), 3.45 (3H, s, H8"), 3.20 (2H, m, H8), 2.21 (3H, s, H11'), 2.02 (3H, s, C$\underline{H}_3$CO), 1.83 (3H, s, C$\underline{H}_3$CO), 1.75 (3H, s, C$\underline{H}_3$CO), 1.71 (3H, s, C$\underline{H}_3$CO), 1.63 (6H, s, H11, H12), 1.25 (3H, s, H6"), 1.05 (3H, s, H7"); $^{13}$CNMR (125 MHz, CD$_3$OD): δ=171.5 (4*CH$_3$$\underline{C}$O), 170.0 (C1), 163.0 (Ca), 161.1 (C2'), 160.8 (C4'), 159.5 (C9'), 159.1 (C2), 152.2 (C7'), 133.7 (C10), 130.9 (C3), 130.1 (C5), 128.5 (C5'), 125.0 (C4), 123.4 (C7), 123.3 (C9), 115.7 (C6), 115.3 (C8'), 112.1 (C10'), 111.8 (C6'), 108.5 (C3') 101.8 (C1'''), 100.2 (C1"), 82.6 (C4"), 80.1 (C5"), 73.0 (C4'''), 72.7 (C5'''), 72.0 (C3'''), 70.8 (C2"), 70.3 (C2'''), 68.0 (C3"), 62.0 (C8"), 61.3 (C6'''), 29.3 (C8), 29.0 (C6"), 26.0 (C11), 23.3 (C7"), 20.5 (4*$\underline{C}$H$_3$CO), 18.0 (C12), 8.7 (C11'). HMBC in dicated that H1'''coupled to C4'. HRMS m/z 943.3366 ([M+H$^+$]$^+$) (Calc. 943.3348).

Synthesis of β-4'-O-galactosyl Novobiocin (3)

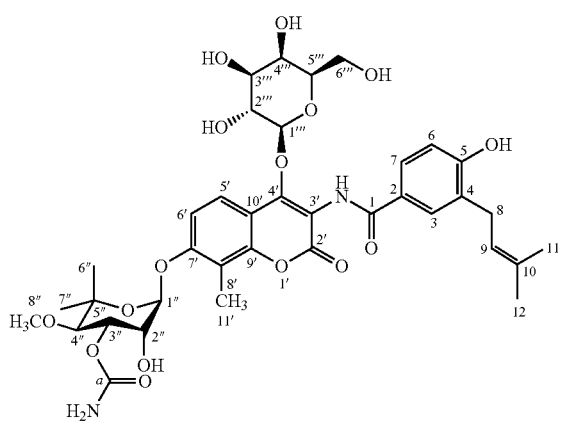

β-4'-O-(2,3,4,6-tetra-acetyl galactosyl) Novobiocin (94 mg, 0.1 mmol) were dissolved in anhydrous MeOH (10 mL). NaOMe (1 mg, 0.02 mmol) was added and stirred for 1 minute at room temperature. Solvent was removed under reduced pressure and purified by HPLC as above gave white power (50 mg, 0.06 mmol, with 65% yield). $^1$H-NMR (500 MHz, CD$_3$OD): δ=7.71 (1H, d, J=8.7 Hz, H5'), 7.67 (1H, d, J=1.8 Hz, H3), 7.62 (1H, dd, J=2.3, 8.4 Hz, H7), 7.02 (1H, d, J=8.6 Hz, H6'), 6.71 (1H, d, J=8.3 Hz, H6), 5.45 (1H, d, J=2.3 Hz, H1''), 5.23 (1H, m, H9), 5.25 (1H, m, H3''), 5.13 (1H, s, H1'''), 4.13 (1H, t, J=2.6 Hz, H2''), 4.23 (1H, m, H6'''), 3.43 (1H, m, H6'''), 4.20 (1H, t, J=4.3 Hz, H5'''), 3.50 (1H, m, H4''), 3.84 (1H, t, J=4.5 Hz, H4'''), 3.46 (3H, s, H8''), 3.73 (1H, m, H3'''), 3.55 (1H, m, H2'''), 3.22 (2H, m, H8), 2.21 (3H, s, H11'), 1.64 (6H, s, H11, H12), 1.25 (3H, s, H6''), 1.07 (3H, s, H7''); $^{13}$CNMR (125 MHz, CD$_3$OD): δ=170.2 (C1), 159.6 (Ca), 159.3 (C2'), 158.3 (C4'), 158.1 (C2), 155.9 (C9'), 153.3 (C7'), 133.1 (C10), 130.7 (C5), 124.6 (C4), 129.1 (C3), 110.4 (C6'), 123.3 (C5'), 123.9 (C9), 127.0 (C7), 115.3 (C6), 114.5 (C8'), 114.1 (C10'), 108.5 (C3') 102.8 (C1'''), 99.9 (C1''), 82.3 (C4''), 79.8 (C5''), 72.5 (C3'''), 65.9 (C4'''), 71.7 (C3''), 71.0 (C2''), 73.3 (C2'''), 62.2 (C8''), 64.5 (C6'''), 76.1 (C5'''), 29.0 (C8), 29.3 (C7''), 26.0 (C11), 22.3 (C6''), 17.9 (C12), 8.8 (C11'). HMBC indicated that H1''' coupled to C4'. HRMS m/z 797.2787 ([M+Na$^+$]$^+$) (Calc. 797.2745).

Example 3

Anti-Proliferative Activity

The anti-proliferative activities of Novobiocin and its derivatives were evaluated using the MTT assay, (Mosmann et al, J. Immunol. Methods 1983, 65 (1-2), 55-63), which measures the relative inhibition of cell proliferation in cells exposed to the compounds, compared to untreated controls. The cell number is estimated colorimetrically based on the transformation of the yellow MTT reagent (3-(4,5-Dimethylthiazol-2-yl)-2,5-diphenyltetrazolium bromide) to a purple formazan dye by mitochondrial enzymes.

Human cell lines derived from ovarian cancer (A2780, ECACC 93112519), lung cancer (A549, ATCC CCL-185), breast cancer (MCF7, ATCC HTB-22), pancreatic cancer (MiaPaCa2, ATCC CRL-1420) and brain cancer (U87MG, ATCC HTB-14), were obtained from the European Collection of Cell Cultures (ECACC, Salisbury, UK). The A2780, A549, MCF7 and MiaPaCa2 cells were grown in Dulbecco's Modified Eagle Medium (DMEM) supplemented with 10% fetal bovine serum (Biosera, UK), 1% L-glutamine and 1% non-essential aminoacids (Gibco, Invitrogen, USA). U87MG cells were grown in Minimal essential medium supplemented with 10% fetal bovine serum (Biosera, UK), 1% L-glutamine, 1% non-essential aminoacids and 1% Sodium piruvate (Gibco, Invitrogen, USA). Cells were grown in a 5% CO$_2$, 95% humidity incubator. In order to determine the IC$_{50}$ of the compounds, i.e. the concentration of compound that leads to a 50% inhibition of cell growth, the cells were seeded in 96 well plates in a volume of 100 μl of medium per well to reach 50-60% confluence on the day of the experiment. The compounds were dissolved in methanol at a maximum concentration of 20 mM, and serial decimal dilutions were prepared in methanol. For each compound and each concentration, 5 μl of the methanol solution were added over the cells, growing in 100 μl of cell culture medium per well (n=6). After 24 h of continuous drug exposure, the growth inhibition was determined using the MTT assay (Lancaster Synthesis Ltd, UK). The amount of dye was quantified spectrophotometrically as absorbance at λ=570 nm (ELx808, Bio-Tek Instruments, Inc.). The IC$_{50}$ values were calculated by a dose-response analysis using the Origin 6.0® software. The values are given in Table 1 below.

TABLE 1

| IC$_{50}$ values | | | | | |
|---|---|---|---|---|---|
| IC50/mM | A2780 | A549 | MCF7 | U87MG | MiaPaCa2 |
| Novobiocin | 0.19 | >1 | >1 | 0.58 | 0.32 |
| Galactosyl_Novobiocin | 0.10 | 0.10 | 0.04 | 0.03 | 0.03 |
| Glucosyl_Novobiocin | 0.13 | 0.06 | 0.01 | 0.02 | 0.01 |

Figure 4:
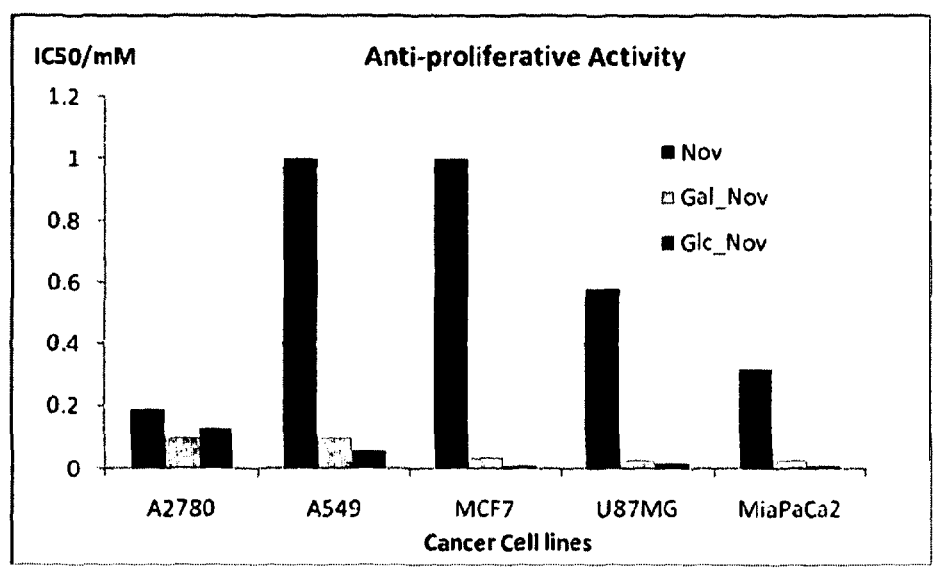
FIG. 4 shows the $IC_{50}$ data from Table 1 (Nov=Novobiocin, Gal_Nov=Galactosyl_Novobiocin, Glc_Nov=Glucosyl_Novobiocin)
Figure 5:
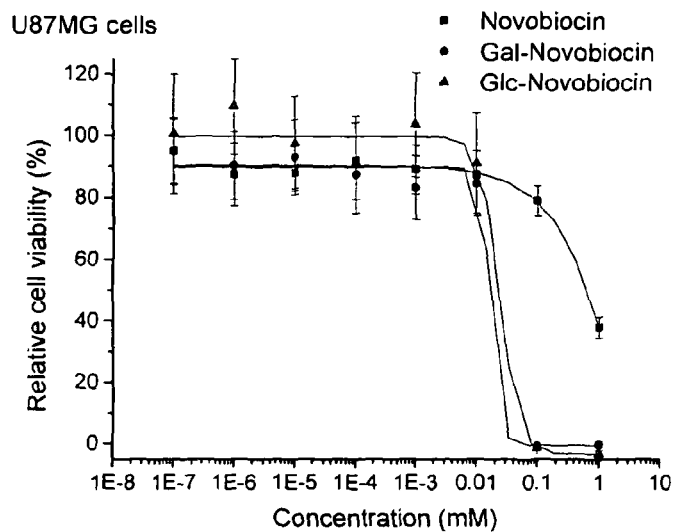
FIG. 5 shows the dose-response curves obtained for the tested compounds in a panel of human cancer cell lines after 24 hours of continuous exposure.

The data are illustrated in FIGS. 4 and 5. FIG. 4 shows the IC$_{50}$ data from Table 1 (Nov=Novobiocin, Gal-Nov=Galactosyl Novobiocin, Glc-Nov=Glucosyl Novobiocin. FIG. 5 shows the dose-response curves obtained for the tested compounds in a panel of human cancer cell lines after 24 hours of continuous exposure.

Example 4

DNA Gyrase Assay

The DNA gyrase assay was performed according to the supplier procedure using novobiocin, glucosyl-novobiocin and galactosyl-novobiocin as inhibitors.

DNA Gyrase (1U) is incubated with relaxed pBR322 (0.5 μg) in a reaction volume of 30 μL at 37°C for 1 hr in TRIS-HCl (35 mM, pH 7.5), KCl (24 Mm), MgCl2 (4 mM), DTT (2 mM), spermidine (1.8 mM), ATP (1 mM), glycerol (6.5%, w/v), albumin (0.1 mg/mL).

After incubation the mixture was deproteinized with equal volumes of chloroformisoamyl alcohol (24:1) and the end point was determined by separating relaxed and supertwisted plasmid pBR322DNA by agarose gel electrophoresis (0.8% agarose with TBE buffer), running without Ethidium Bromide. After the run the gel is soaked, in tank buffer containing Ethidium Bromide, for 1 and half hours.

The MIC for novobiocin is about 1 μM which is consistent with literature values. Both glucosyl-novobiocin and galactosyl-novobiocin performed in a similar fashion with MIC values of 3 μM.

Example 5

Activity of Novobiocin and Novobiocin Derivatives Against *Escherichia coli*

Method:

The MICs of novobiocin and novobiocin derivatives were determined by micro-broth dilution technique in cation-adjusted Mueller-Hinton broth and with an *E. coli* inoculum of 5×10$^5$ CFU/ml. Microtitre plates were incubated aerobically at 37° C. and read after one and four days. The concentration range tested was 128 to 0.5 μg/ml. A cell permeabilising agent, polyethylenimine (PEI) was used to assess the influence of cell membrane (and associated structures) as a barrier to novobiocin entry into the cell. Isopropyl β-D-1-thiogalactopyranoside (100 μM) was used to induce β-glycosidase and β-galactosidase expression from plasmids pSsβG and pBCSK, respectively. These enzymes can release the native drugs from the conjugates.

Figure 6:
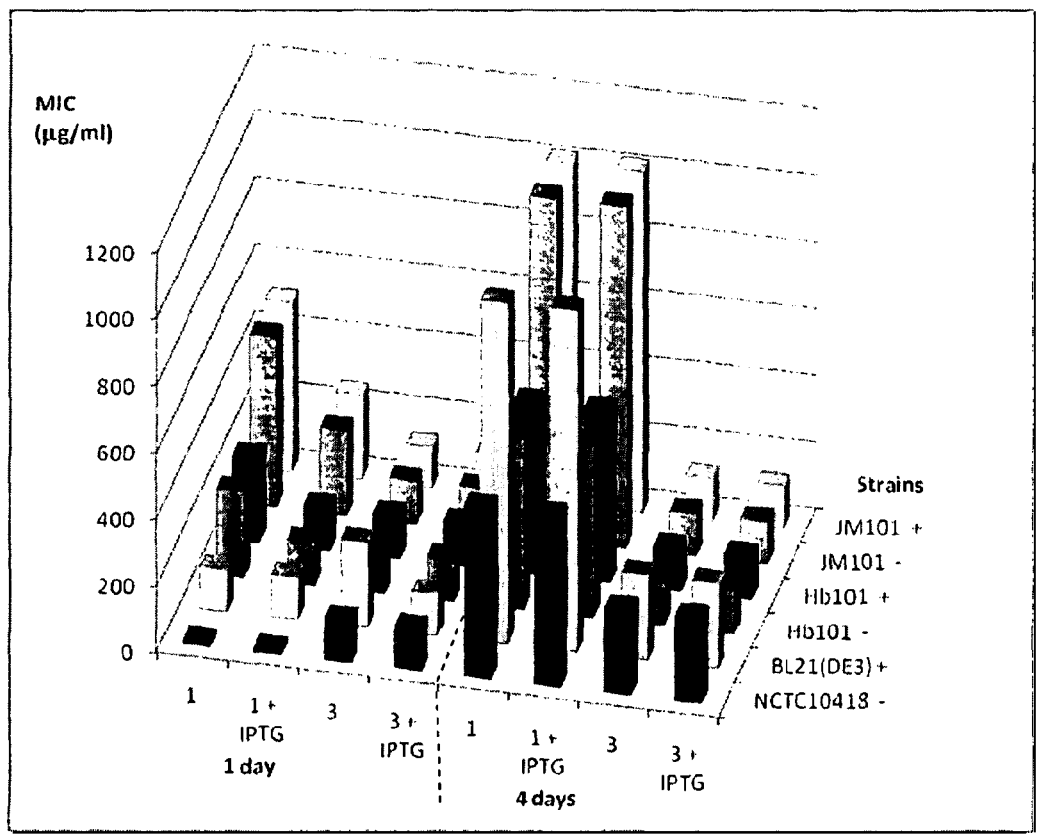
FIG. 6 shows the results of the MIC test, generated from the M.I.C. data of novobiocin and galactosyl_novobiocin against selected microorganisms.

FIG. 6 illustrates the results of the MIC test, generated from the M.I.C. data of novobiocin and glucosyl-novobiocin against selected microorganisms. Strains with (+) indicate there are transferred galactosidase plasmids, (−) indicate no plasmids. Data to the left of the base are MIC in 1 day while those to the right of the base are 4 days results. MICs over maximum (512 μg/ml) are illustrated with the next level (1024 μg/ml) as there are some MICs at 512 μg/ml.

Figure 7:
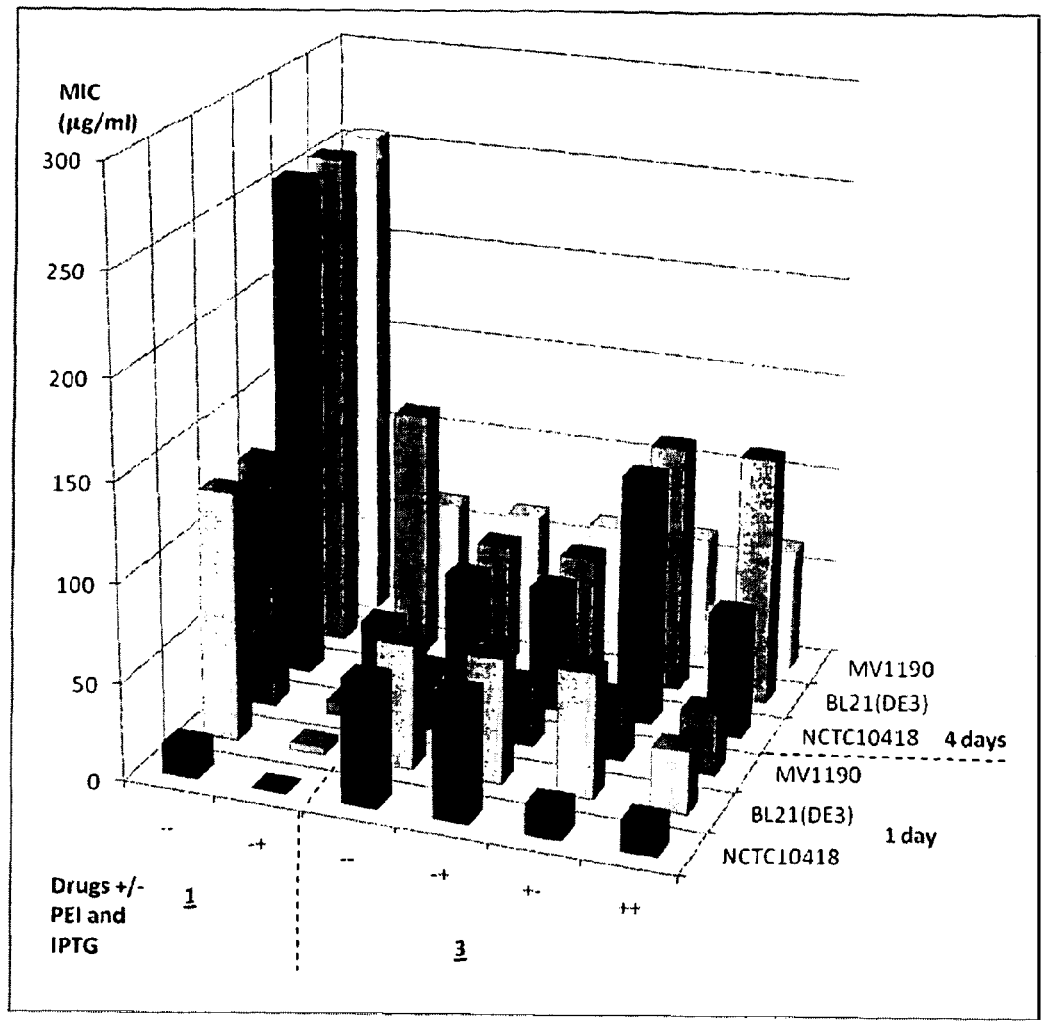
FIG. 7 shows the results of the tests for the influence of polyethylenimine (PEI) and plasmids expressing β-glucosidase on the activities of novobiocin and glycosyl_novobiocins against *E-coli*.

FIG. 7 illustrates the results of the tests for the influence of a plasmid expressing a β-glucosidase on the activities of novobiocin and novobiocin-Gal against *E-coli*. Compound 1 is novobiocin and 3 is galactosyl-novobiocin. X-axial indicates the drugs and conditions tested: −−: PEI (−), IPTG (−); −+: PEI (−), IPTG (+); +−: PEI (+), IPTG (−); ++: PEI (+), IPTG (+). Colour: data to the left of the figure are the results of novobiocin (1) while front left show the results from 1 day test and the back left results from 4 days test; data to the right of the figure are the results of galactosyl_novobiocin (3), while front right indicates result from 1 day test and far right from 4 days test. MICs over maximum (128 μg/ml) are illustrated with the next level (256 μg/ml) as there are some MICs at 128 μg/ml.

CONCLUSIONS

Glycosylated novobiocin has increased anticancer activity up to 100-fold against breast, brain, prostrate, lung and ovarian cancers. Glycosylation does not appear to influence binding to DNA gyrase.

In the presence of PEI, novobiocin exhibited increased activity (16-32 fold) against *Escherichia coli*. This was independent of whether β-galactosidase was produced or not and suggests that, in contrast to novobiocin, the outer membrane was not acting as an effective barrier against the galactosyl derivative. Differences in activities in the presence of PEI probably reflect variations in the mode of action between the native drug and galactosyl derivative. This is supported by the observation that, unlike the bacteriostatic agent novobiocin, prolonged incubation (up to 4 days) in the presence of galactosyl-novobiocin did not lead to re-growth at concentrations above the MIC, which may indicate a bactericidal mode of action.

Glycosyl_novobiocin (2) was less toxic than its precursor; an observation consistent with the glycoslation effect seen with other antimicrobial agents.

Example 6

A study was conducted with the aim of finding UGTs or UGT mutants, whihx can use UDP-galactose as a sugar donor for certain aminocoumarins.

A summary of the results is shown below:

Site directed mutagenesis was conducted in order to form a number of D to E and/or Q to H mutants. The following mutants were synthesised:
73C5D397E (+)
73C6D397E (+)
73C1D393E (−)
73B4Q374H (−)
73B3Q397H (−)
73C1Q394H (−)
88A1Q384H (+)
71B8Q390H (−)
76E4Q375H (−)
73C1D393EQ394H (+)

The symbol "+" means that the mutants could use UDP-Gal as new donor and "−" denotes a negative result.

The ability to use UDP-glucose and UDP-galactose as a donor for novobiocin was tested using mass spectrometry (by searching for a peak relating to the glycosyated novobiocin). It was found that all could use UDP-glucose as a donor. It was also found that those mutants marked with a "(+)" could use UDP-galactose as a donor.

The invention claimed is:

1. An aminocoumarin compound glycosylated at the 4-OH position of the core of the aminocoumarin compound having the formula

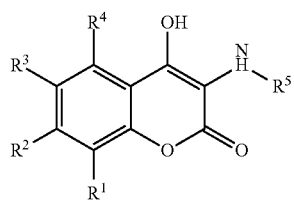

wherein $R^1$, $R^3$ and $R^4$ are each independently selected from H, OH, $C_{1-20}$ alkyl, $C_{1-20}$ alkenyl, amino, or a halogen;

$R^2$ is an optionally substituted sugar moiety;

$R^5$ is selected from aryl, heteroaryl, $C_{1-20}$ alkyl, $C_{1-20}$ alkenyl, H, or $C(=O)R^6$, wherein $R^6$ is selected from the same groups as $R^5$ or is halo, amino, or OH; and wherein X is a sugar selected from glucose and galactose.

2. An aminocoumarin compound according to claim 1 for use in therapy.

3. An aminocoumarin compound according to claim 2 for use as an antibiotic.

4. An aminocoumarin compound according to claim 2 for use in anticancer treatment.

5. A pharmaceutical composition comprising an aminocoumarin compound according to claim 1 and one or more pharmaceutically acceptable excipients.

* * * * *